(12) United States Patent
Grossman et al.

(10) Patent No.: US 11,759,634 B2
(45) Date of Patent: *Sep. 19, 2023

(54) METHODS AND APPARATUS FOR STIMULATION OF BIOLOGICAL TISSUE

(71) Applicant: Massachusetts Institute of Technology, Cambridge, MA (US)

(72) Inventors: Nir Grossman, Lorrach (DE); David Bono, Wellesley, MA (US); Edward Boyden, Chestnut Hill, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 365 days.

This patent is subject to a terminal disclaimer.

(21) Appl. No.: 17/140,022

(22) Filed: Jan. 1, 2021

(65) Prior Publication Data

US 2021/0121693 A1    Apr. 29, 2021

Related U.S. Application Data

(63) Continuation of application No. 16/221,582, filed on Dec. 17, 2018, now Pat. No. 10,905,878, which is a
(Continued)

(51) Int. Cl.
*A61N 1/36* (2006.01)
*A61N 1/05* (2006.01)

(52) U.S. Cl.
CPC ....... *A61N 1/36017* (2013.01); *A61N 1/0529* (2013.01); *A61N 1/36014* (2013.01);
(Continued)

(58) Field of Classification Search
CPC .............. A61N 1/0529; A61N 1/0531; A61N 1/0534; A61N 1/323; A61N 1/36014;
(Continued)

(56) References Cited

U.S. PATENT DOCUMENTS 1,425,743 A    8/1922    Baruch
2,622,601 A    12/1952   Nemec
(Continued)

FOREIGN PATENT DOCUMENTS

WO    2013192582 A1    12/2013

OTHER PUBLICATIONS

Correa, J. et al., Effects of the carrier frequency of interferential current on pain modulation in patients with chronic nonspecific low back pain: a protocol of a randomised controlled trial; published in BMC Musculoskeletal Disorders 2013, 14:195 (2013).
(Continued)

*Primary Examiner* — George Manuel
(74) *Attorney, Agent, or Firm* — Smith Baluch LLP

(57) ABSTRACT

In illustrative implementations of this invention, interferential stimulation is precisely directed to arbitrary regions in a brain. The target region is not limited to the area immediately beneath the electrodes, but may be any superficial, mid-depth or deep brain structure. Targeting is achieved by positioning the region of maximum envelope amplitude so that it is located at the targeted tissue. Leakage between current channels is greatly reduced by making at least one of the current channels anti-phasic: that is, the electrode pair of at least one of the current channels has a phase difference between the two electrodes that is substantially equal to 180 degrees. Pairs of stimulating electrodes are positioned side-by-side, rather than in a conventional crisscross pattern, and thus produce only one region of maximum envelope amplitude. Typically, current sources are used to drive the interferential currents.

20 Claims, 20 Drawing Sheets

Related U.S. Application Data continuation of application No. 15/512,556, filed on Mar. 19, 2017, now Pat. No. 10,173,061.

(60) Provisional application No. 62/061,349, filed on Oct. 8, 2014.

(52) U.S. Cl.
CPC ..... *A61N 1/36125* (2013.01); *A61N 1/36146* (2013.01); *A61N 1/36185* (2013.01); *A61N 1/36034* (2017.08)

(58) Field of Classification Search
CPC ............ A61N 1/36017; A61N 1/36025; A61N 1/36034; A61N 1/36082; A61N 1/36125; A61N 1/36146; A61N 1/36185
See application file for complete search history.

(56) References Cited

U.S. PATENT DOCUMENTS

| | | | |
|---|---|---|---|
| 3,096,768 A | 7/1963 | Griffith, Jr. | |
| 3,774,620 A | 11/1973 | Hansjurgens | |
| 3,895,639 A | 7/1975 | Rodler | |
| 3,951,134 A | 4/1976 | Malech | |
| 3,958,577 A | 5/1976 | Rodler | |
| 4,023,574 A | 5/1977 | Nemec | |
| 4,071,033 A | 1/1978 | Nawracaj et al. | |
| 4,153,061 A | 5/1979 | Nemec | |
| 4,280,504 A | 7/1981 | Rodler | |
| 4,401,121 A | 8/1983 | Rodler | |
| 4,503,863 A | 3/1985 | Katims | |
| 4,848,347 A | 7/1989 | Hall | |
| 5,269,304 A | 12/1993 | Matthews | |
| 5,324,317 A | 6/1994 | Reiss | |
| 5,512,057 A | 4/1996 | Reiss et al. | |
| 5,540,735 A | 7/1996 | Wingrove | |
| 5,573,552 A | 11/1996 | Hansjurgens | |
| 5,776,173 A | 7/1998 | Madsen, Jr. et al. | |
| 5,817,138 A | 10/1998 | Suzuki | |
| 6,246,912 B1 | 6/2001 | Sluijter et al. | |
| 6,584,358 B2 | 6/2003 | Carter et al. | |
| 10,173,061 B2 | 1/2019 | Grossman et al. | |
| 10,905,878 B2 | 2/2021 | Grossman et al. | |
| 2006/0149337 A1 | 7/2006 | John | |
| 2007/0156202 A1* | 7/2007 | Zierhofer | A61N 1/36038 607/57 |
| 2007/0191906 A1 | 8/2007 | Iyer et al. | |
| 2010/0114258 A1 | 5/2010 | Donofrio et al. | |
| 2014/0213843 A1 | 7/2014 | Pilla et al. | |

OTHER PUBLICATIONS

De Domenico, G., Pain Relief With Interferential Therapy, published in Australian Journal of Physiotherapy, vol. 28, Issue 3, Jun. 1982, pp. 14-18 (1982).

Fuentes, J., et al., Effectiveness of Interferential Current Therapy in the Management of Musculoskeletal Pain: A Systematic Review and Meta-Analysis; published in Physical Therapy, Sep. 2010; 90(9):1219-38 (2010).

Goats, G., Interferential current therapy; published in Br J Sports Med. Jun. 1990; vol. 24, No. 2, pp. 87-92 (1990).

Palmer, S., et al., Alteration of interferential current and transcutaneous electrical nerve stimulation frequency: effects on nerve excitation; published in Physical Medicine and Rehabilitation, vol. 80, Issue 9, pp. 1065-1071 (Sep. 1999).

\* cited by examiner

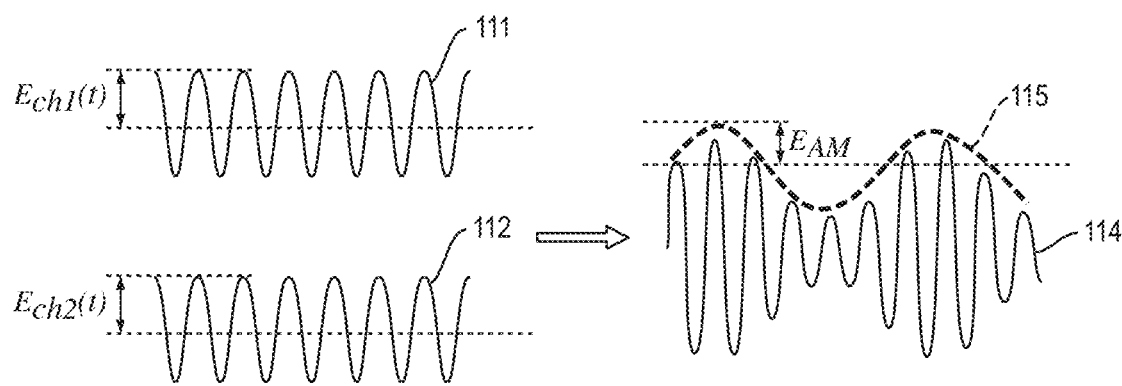
FIG. 1A
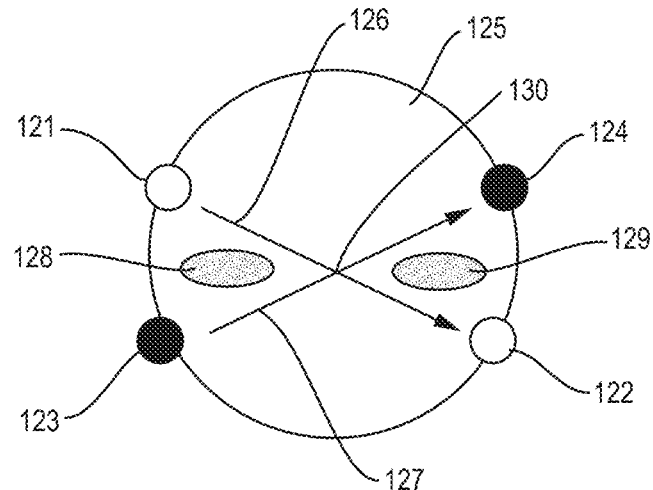
FIG. 1B
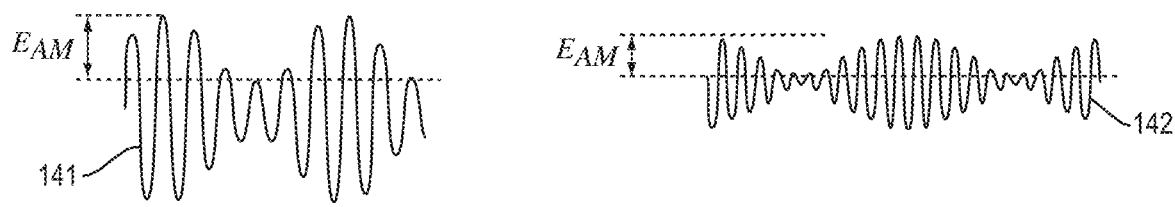
FIG. 1C
FIG. 1D

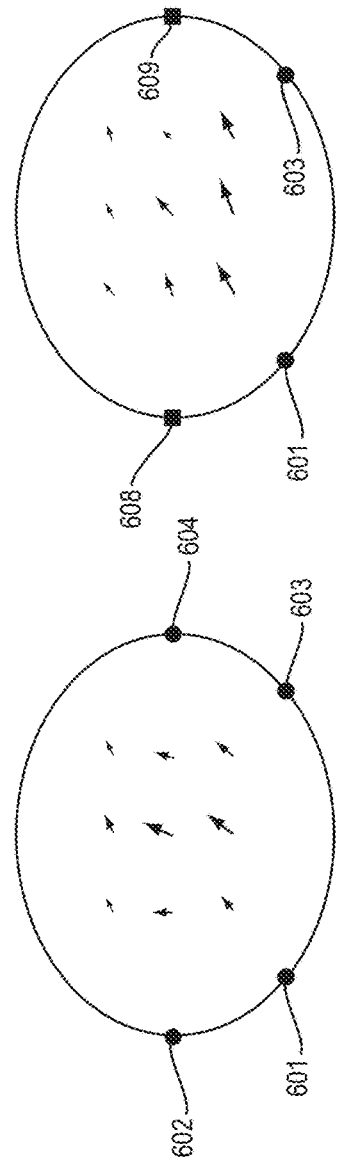
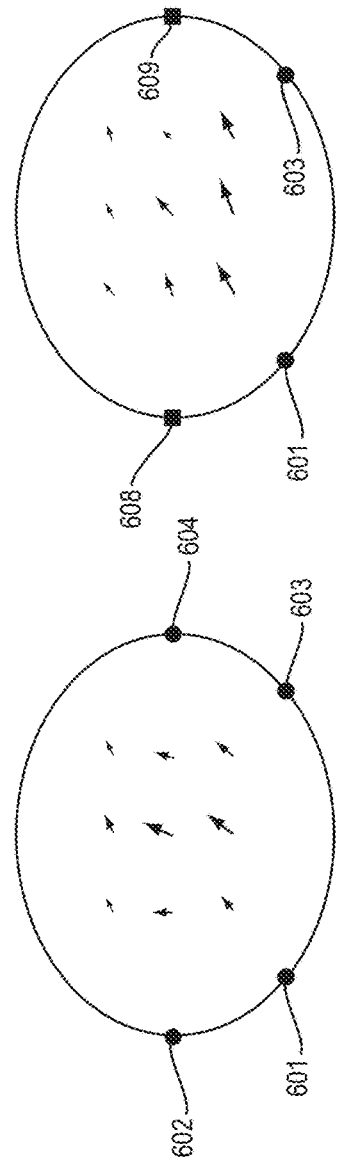
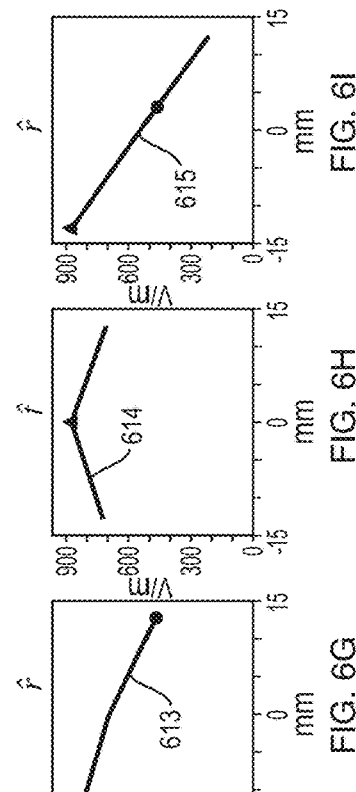
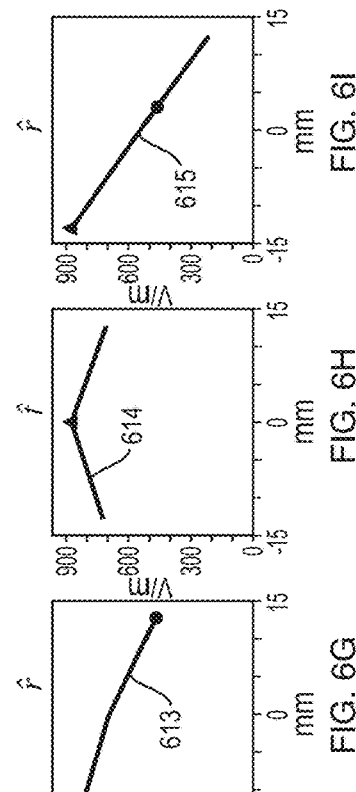
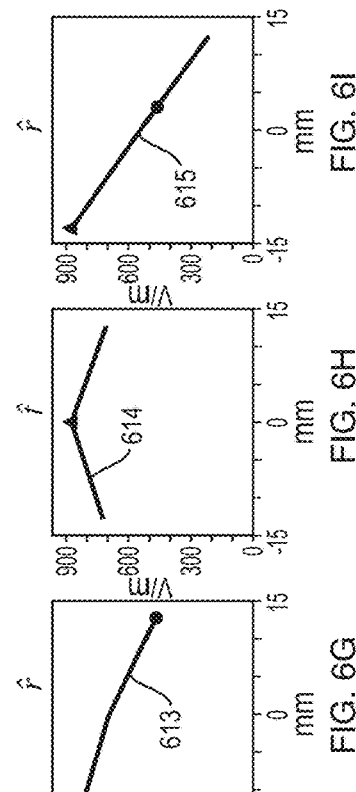
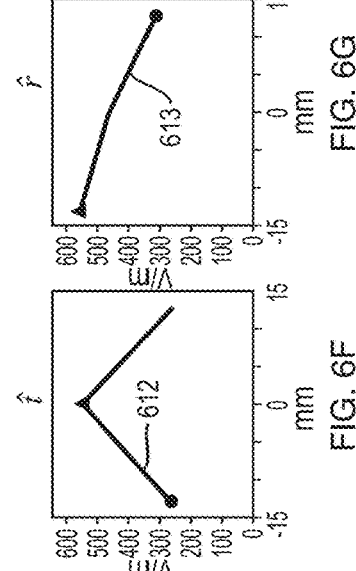
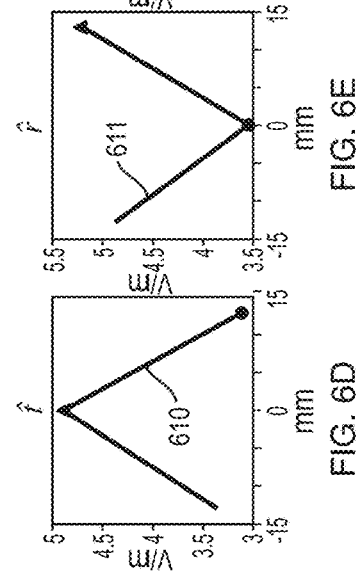
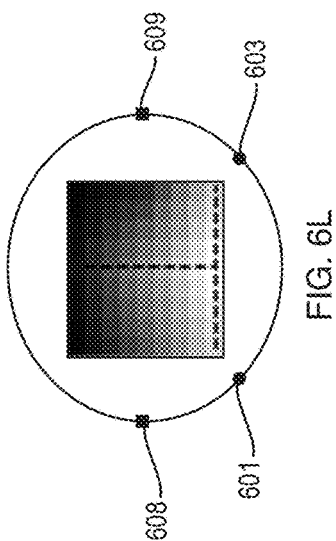
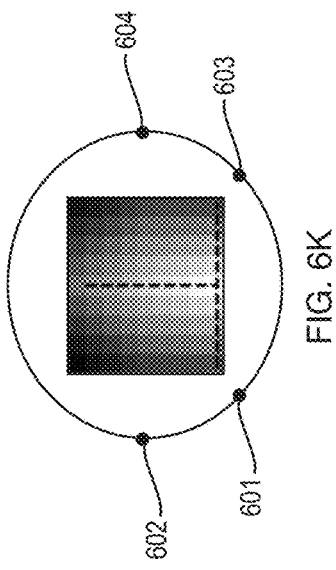
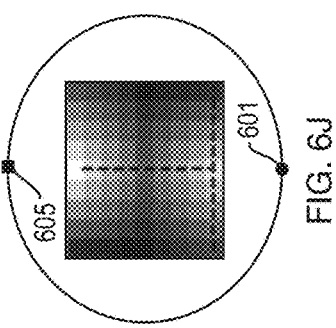
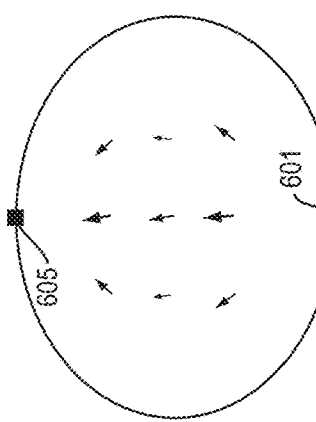

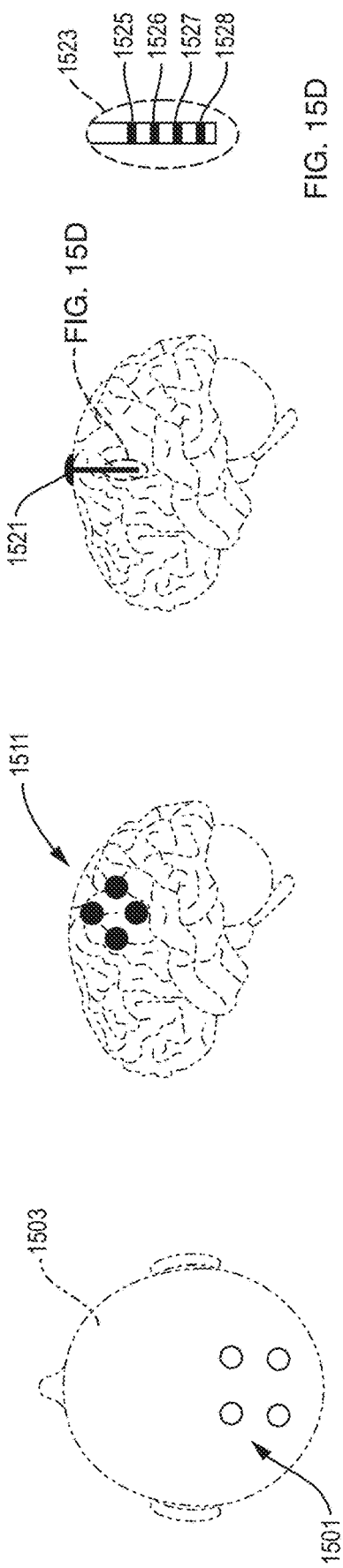

METHODS AND APPARATUS FOR STIMULATION OF BIOLOGICAL TISSUE

RELATED APPLICATIONS

This application is a continuation of U.S. patent application Ser. No. 16/221,582 filed Dec. 17, 2018, which is a continuation of U.S. patent application Ser. No. 15/512,556 filed Mar. 19, 2017, which claims the benefit of U.S. Provisional Patent Application No. 62/061,349, filed Oct. 8, 2014 (the "Provisional"). The entire disclosure of the Provisional is incorporated herein by reference.

FIELD OF TECHNOLOGY

The present invention relates generally to stimulation of biological tissue, including interferential stimulation of a brain.

SUMMARY

In illustrative implementations of this invention, interferential stimulation is precisely directed to arbitrary regions in a brain. The region targeted is not limited to the area immediately beneath the electrodes, but may be any superficial, mid-depth or deep brain structure. For example, in some use scenarios of this invention, interferential stimulation is precisely targeted at a deep brain structure, such as the thalamus, hypothalamus, amygdala, or hippocampus. In other use scenarios, interferential stimulation is precisely targeted on a superficial or mid-depth region of the cortex. In yet other use scenarios, interferential stimulation is precisely targeted on both a superficial brain structure and deep brain structure simultaneously.

Conventional interferential current (IFC) devices and methods are not able to achieve this targeting, because they suffer from at least four flaws:

First, targeting by conventional IFC is based on a misconception: It is erroneously believed that maximum cell response occurs in regions where the modulation index of the amplitude-modulated (AM) waveform approaches 100%. In other words, the misconception is that the greater the interference between the two original waveforms that create the AM waveform, the better the interferential therapy works. Thus, based on this misconception, conventional IFC tries to position the region of maximum interference (i.e., where the amplitudes of the two original waveforms that form the AM wave are closest to being equal) at the tissue structure that is the target of the attempted stimulation.

This belief is incorrect. In fact, the maximum cell response to interferential stimulation occurs in the region where the envelope amplitude (as defined herein) of the AM waveform is greatest. The region where the envelope amplitude is greatest does not necessarily coincide with the region of maximum interference, and is often quite different. Examples of envelope amplitude $E_{AM}$ are shown in FIGS. 1A, 1C and 1D.

Second, conventional IFC suffers from significant current leakage between the two current channels that create the interferential effect. An IFC device typically uses two pairs of stimulating electrodes. Each electrode pair is a current channel that creates an electric field. The interference of the two electric fields produces the AM waveform that stimulates cells in interferential therapy. Unfortunately, in conventional IFC, substantial current leakage occurs between the two channels—for example, in some cases, 20% or more of the current across one electrode pair is due to the electric waveform created by the other electrode pair. This crosstalk between current channels may cause the spatial position of interference regions to shift in an undesirable or uncontrolled way. For example, because current from one electrode pair is flowing into the other electrode pair, cell stimulation due to an AM waveform may occur very near the electrodes, even if stimulation is desired to occur at a position remote from the electrodes. This leakage between currents occurs because both pairs of electrodes are electrically connected to the same conductive load—the tissue of the subject being stimulated. In some existing IFCs, transformers have been used to isolate currents. However, transformers tend to be bulky.

Third, in conventional IFC, electrode placement is limited. In conventional IFC, the four stimulating electrodes are positioned in a crisscross pattern, in which each electrode is located at a corner of a rectangle (typically, a square). Thus, the line segment that joins the electrodes of one electrode pair is one diagonal of the rectangle, and the line segment that joins the electrodes of the other electrode pair is the other diagonal of the rectangle. These two diagonals cross each other, forming an X (crisscross) pattern. The electrodes are positioned so that the target tissue region is located at, or beneath, the center of the rectangle where the two crisscrossing diagonals intersect. This crisscross pattern is consistent with (and perhaps was originally motivated by) the misconception described above: in this configuration, the region of maximum interference typically would occur (absent the spatial inaccuracies caused by current leakage) at the center of the rectangle where the two diagonals intersect. Unfortunately, this conventional electrode placement is not suited for targeting some tissue regions, such as deep brain structures remote from the stimulating electrodes. For example, it is typically impossible to position electrodes on the skin in a rectangular pattern such that the hypothalamus (a deep brain structure) is located at the center of the rectangle.

Fourth, in many conventional IFC devices, voltage sources are used to drive the current channels. Unfortunately, the amount of current delivered by a voltage source depends on the impedance of the electrical load. This problem is exacerbated where the conductive load is a brain, because impedance varies widely in different brain structures, making it difficult to deliver a precisely regulated current amount with voltage sources. This in turn makes it difficult to precisely control the spatial position of the interferential stimulus in the brain.

In illustrative embodiments of this invention, a novel interferential stimulation technology overcomes these four hurdles as follows:

First, in illustrative embodiments, targeting is based on achieving a desired envelope amplitude at targeted tissue locations. For example, in some cases, the region of maximum envelope amplitude is positioned at the specific brain structure being targeted. Or, for example, a larger region may be targeted, and the interference tuned such that the envelope amplitude is simultaneously above a certain threshold in all parts of the targeted region.

Second, in illustrative embodiments, currents are isolated by making at least one of the current channels anti-phasic: that is, the electrode pair of at least one of the current channels has a phase difference between the two electrodes that is substantially equal to 180 degrees. This dramatically reduces current leakage between the two current channels. For example, in a prototype of this invention, current leakage between the two current channels has been reduced such that only 4% of the current across one electrode pair is due to the electric field created by the other current channel. Thus in illustrative embodiments, the anti-phasic current channel(s) greatly ameliorate current leakage, which in turn allows the interferential device to more precisely position the region in which the envelope amplitude is at a desired magnitude.

Third, in illustrative embodiments, stimulating electrodes are positioned in a wide variety of spatial configurations, including positions in which the electrodes are not in rectangular (or square) configuration. For example, in some embodiments of this invention: (a) the stimulating electrodes are positioned in a semicircle, or circle, or line; or (b) the stimulating electrodes are positioned such that the distance between electrodes of one electrode pair (current channel) is different than the distance between electrodes of the other electrode pair (current channel) or is different than the distance between the two electrode pairs; or (c) the stimulating electrodes are positioned side-by-side, rather than in a crisscross pattern. Thus, in illustrative embodiments, the positioning of electrodes is adaptable to the structure being stimulated, and may be selected so as to control the spatial position of regions in which the envelope amplitude is above a given threshold.

Fourth, in illustrative embodiments, current sources are used to drive the interferential currents, rather than voltage sources. An advantage of a current source is that the current delivered does not, within the source's compliance voltage range, depend on the impedance of the load. Thus, the amount of current can be precisely controlled, despite the anistropic impedance of the brain. This, in turn, facilitates precise interferential targeting, because the spatial position of a region with a given envelope amplitude depends in part on the magnitude of the currents in the two interferential current channels.

This invention is not limited to stimulation of the brain, but has practical advantages in a wide variety of use cases. Among other things, in illustrative embodiments of this invention, interferential stimulation may be precisely targeted at any deep or superficial region of the body. For example, in some use scenarios of this invention, interferential stimulation is targeted at particular regions of the heart, or at the pineal gland deep inside the cranium, or at the spinal cord or other nerves, or at the digestive tract, or at reproductive tissue, or at a muscle.

This invention is not limited to interferential stimulation. Among other things, current isolation using an anti-phasic current channel may be employed to simultaneously deliver stimulation at different frequencies to different tissue regions, in such a manner that the tissue responds to the original waveforms, and not to the AM waveform created by interference.

The description of the present invention in the Summary and Abstract sections hereof is just a summary. It is intended only to give a general introduction to some illustrative implementations of this invention. It does not describe all of the details and variations of this invention. Likewise, the descriptions of this invention in the Field of Technology section and Field Of Endeavor section are not limiting; instead they each identify, in a general, non-exclusive manner, a technology to which exemplary implementations of this invention generally relate. Likewise, the Title of this document does not limit the invention in any way; instead the Title is merely a general, non-exclusive way of referring to this invention. This invention may be implemented in many other ways.

In some cases, the stimulating electrodes are arranged in a

FIGS. 2A, 2B, 2C, 2D, 2E, 2F, 2G and 2H show neural responses to a time-varying electric field.

Figure 3:
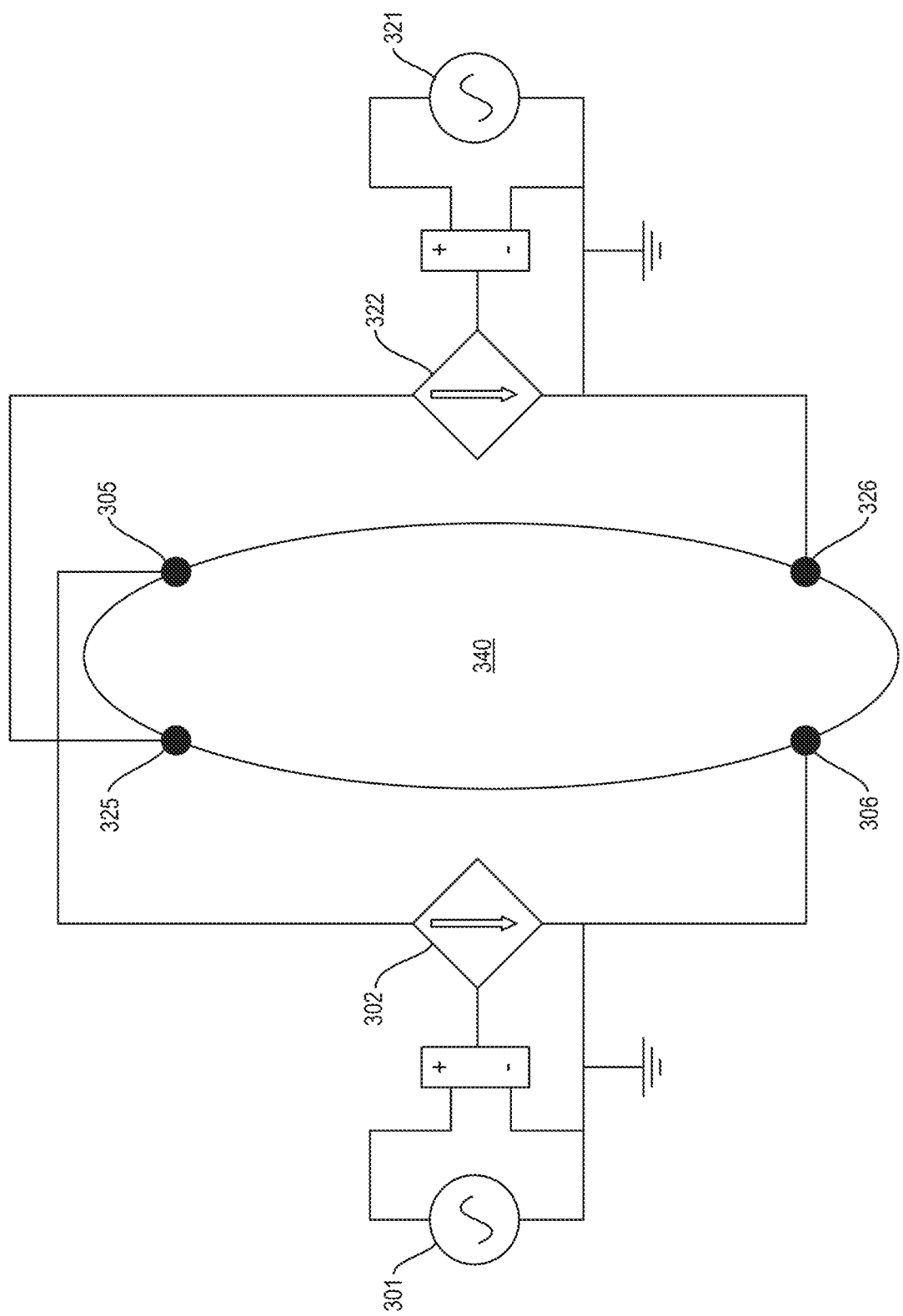

FIG. 3 shows a conventional (prior art) apparatus for applying multiple currents to a common conductive load.

Figure 4A:
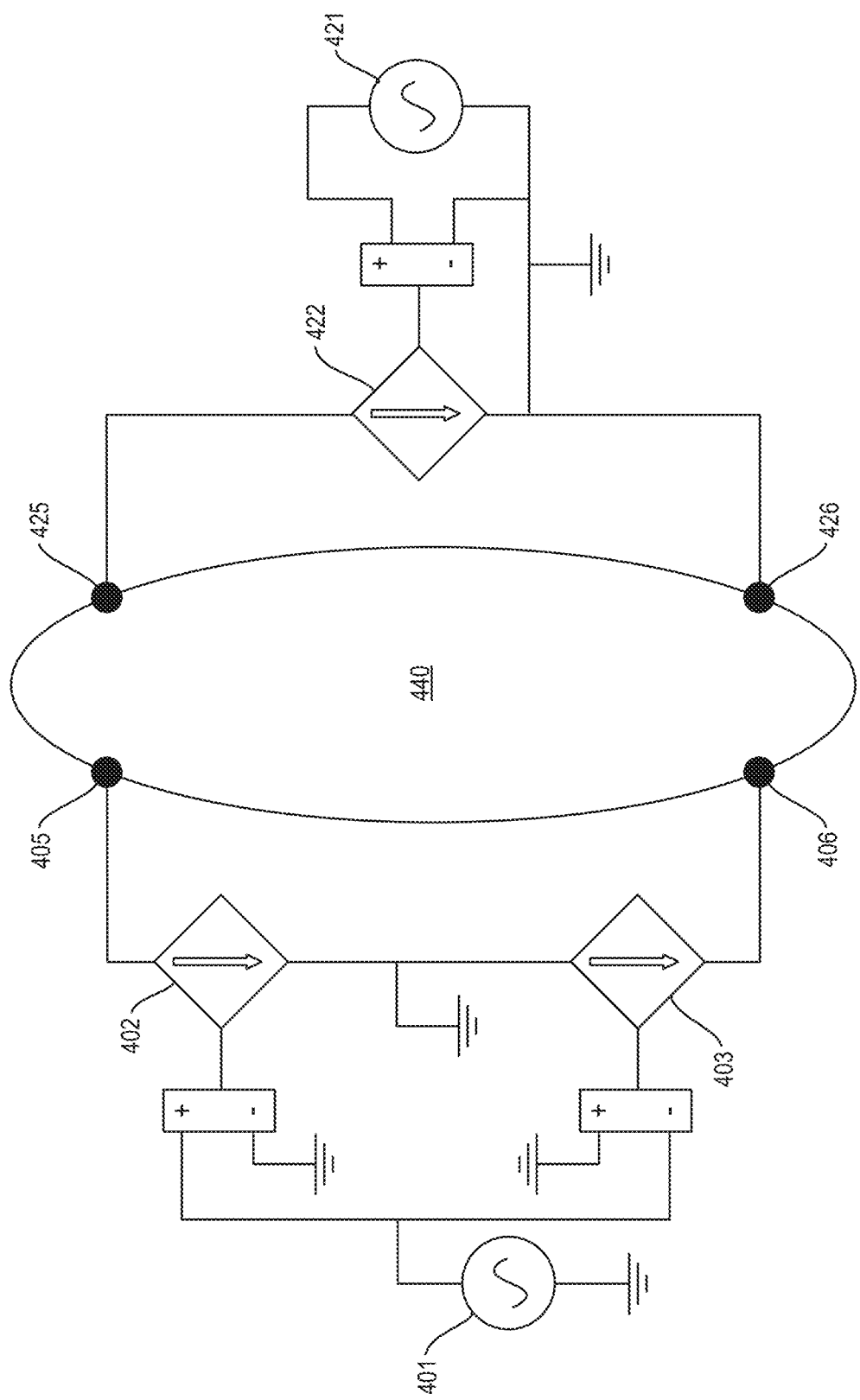
Figure 4B:
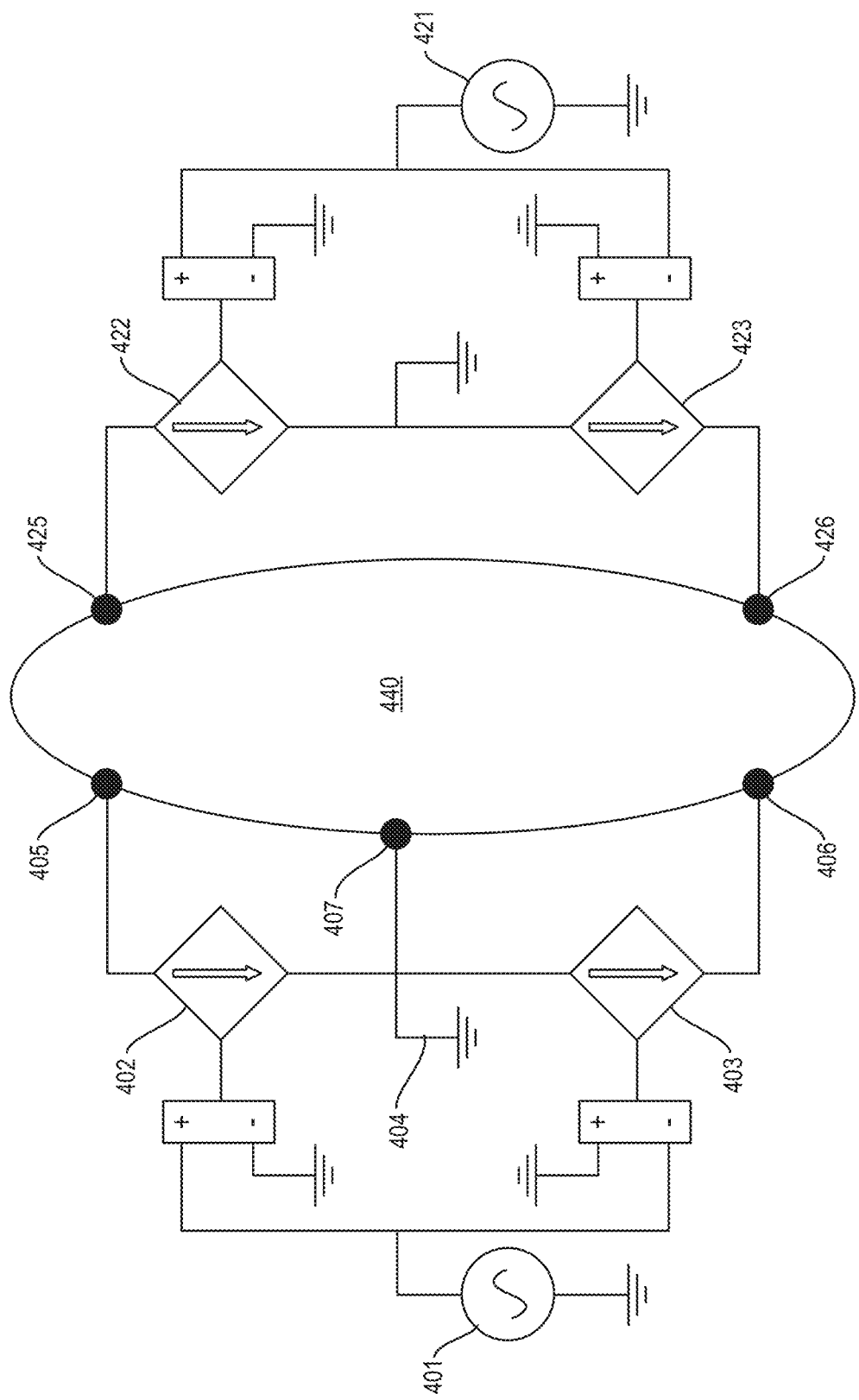
Figure 4C:
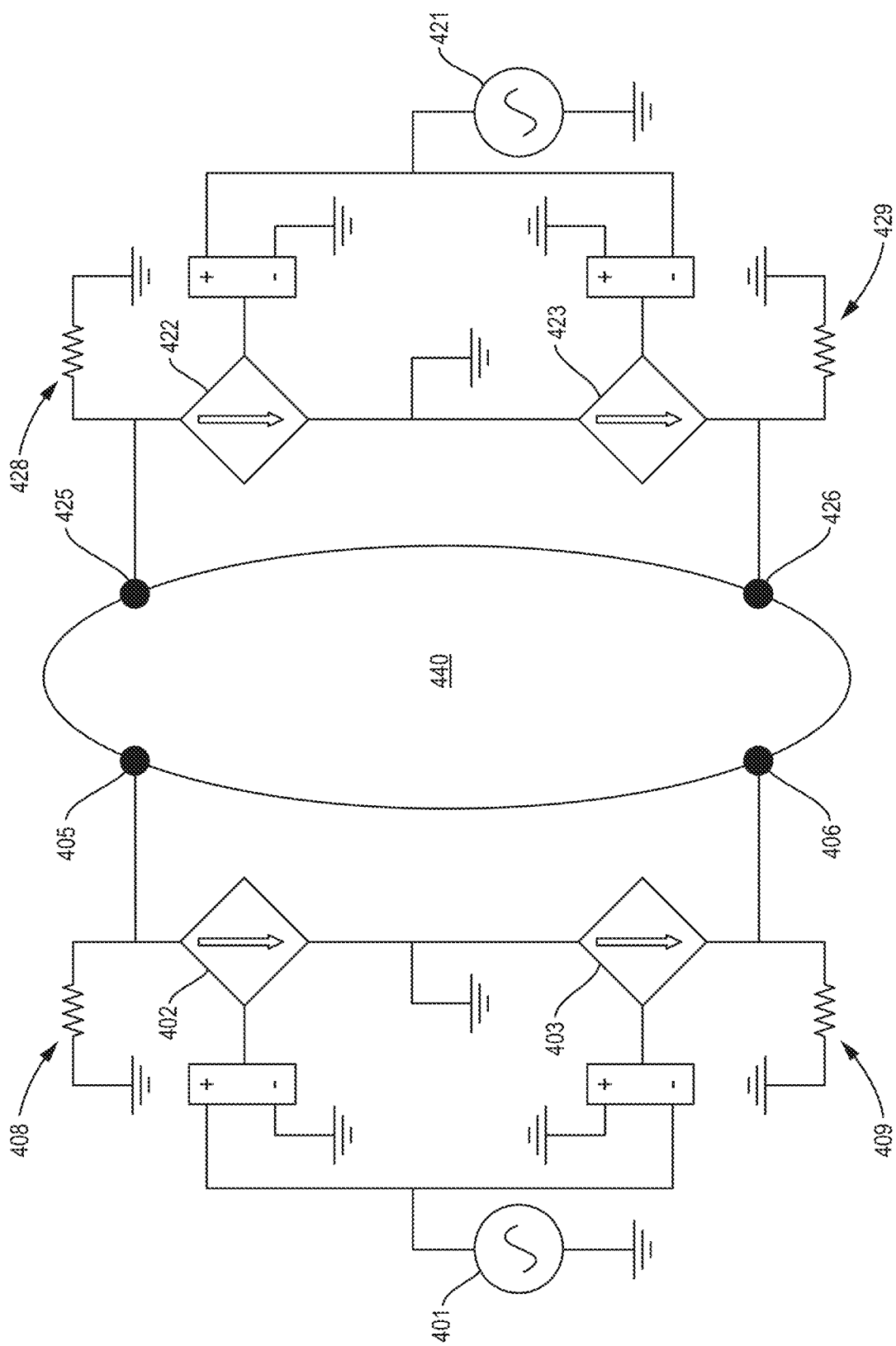

FIGS. 4A, 4B and 4C each show examples of an anti-phasic current drive for applying isolated currents to a common conductive load.

Figure 4D:
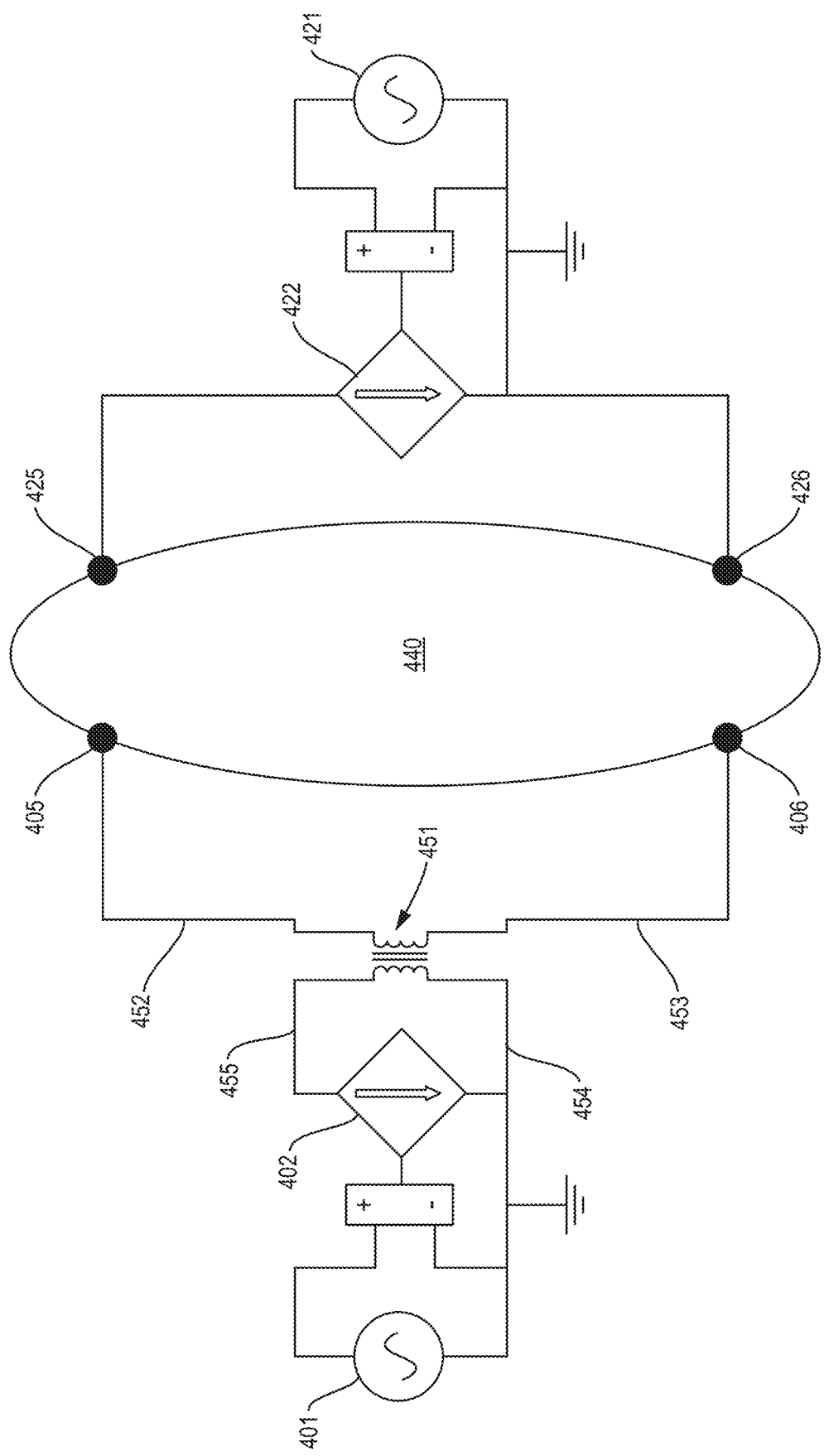

FIG. 4D shows an example of a current drive that includes an isolation transformer, and that is configured to apply isolated currents to a common conductive load.

FIGS. 5A, 5B, 5C, 5D, 5E, 5F, 5G, 5H, 5I, 6A, 6B, 6C, 6D, 6E, 6F, 6G, 6H, and 6I show measured values of electrical fields in a 2D phantom. FIGS. 5J, 5K, 5L, 6J, 6K, and 6L each show a 2D grayscale amplitude map of an electrical field.

Figure 7:
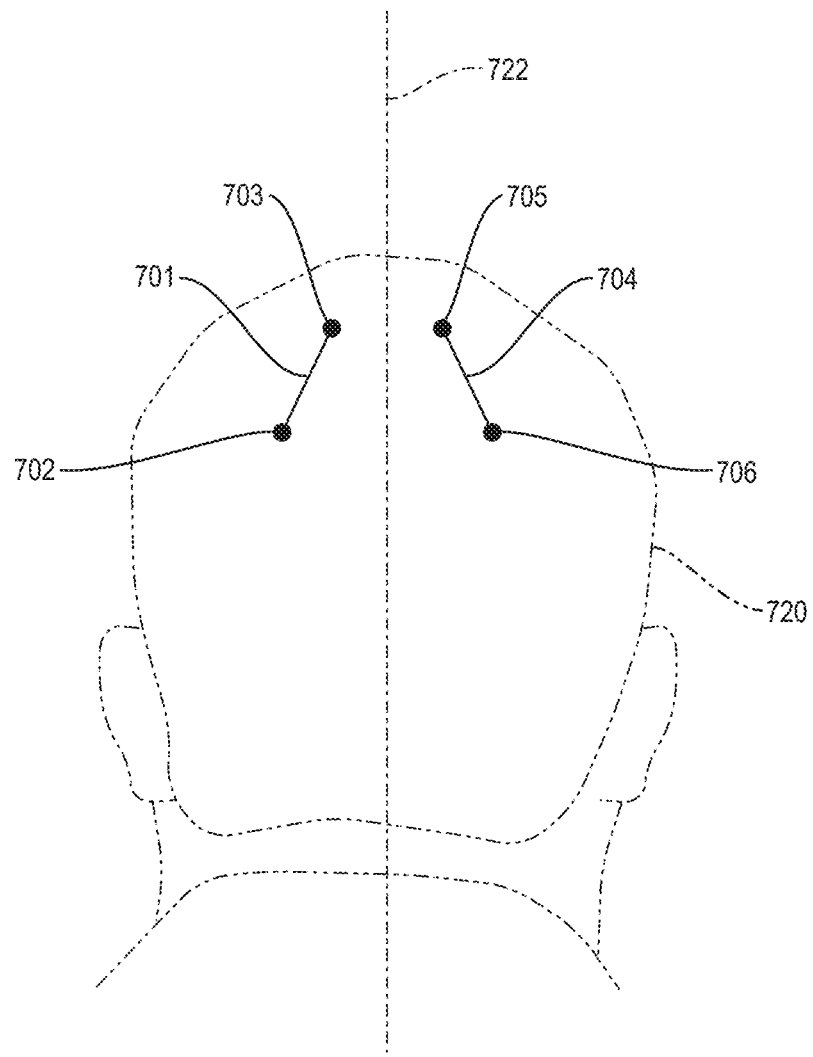

FIG. 7 shows an example of side-by-side positioning of electrode pairs.

Figure 8:
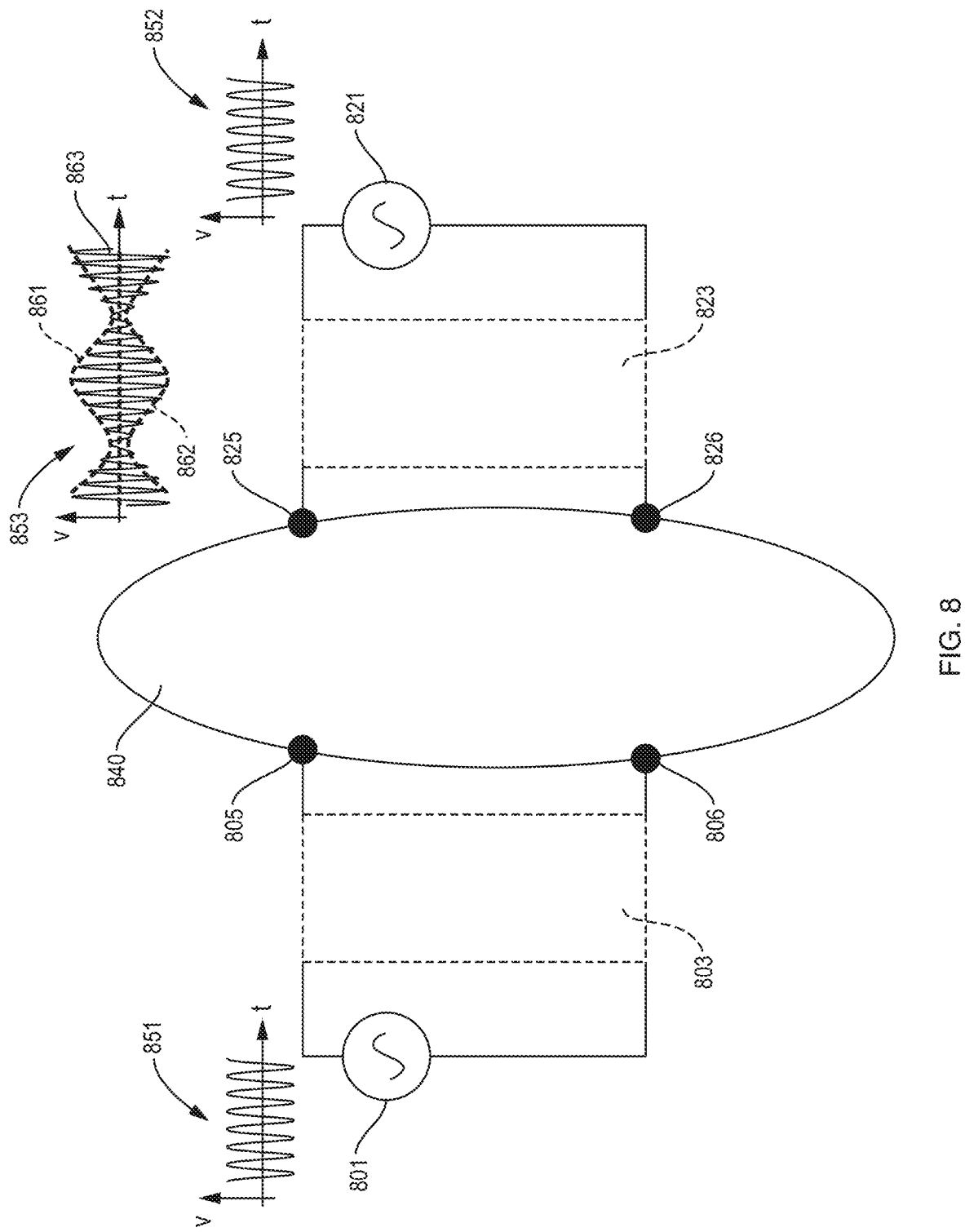

FIG. 8 shows a conventional (prior art) zero-mean envelope AM electric field.

Figure 9:
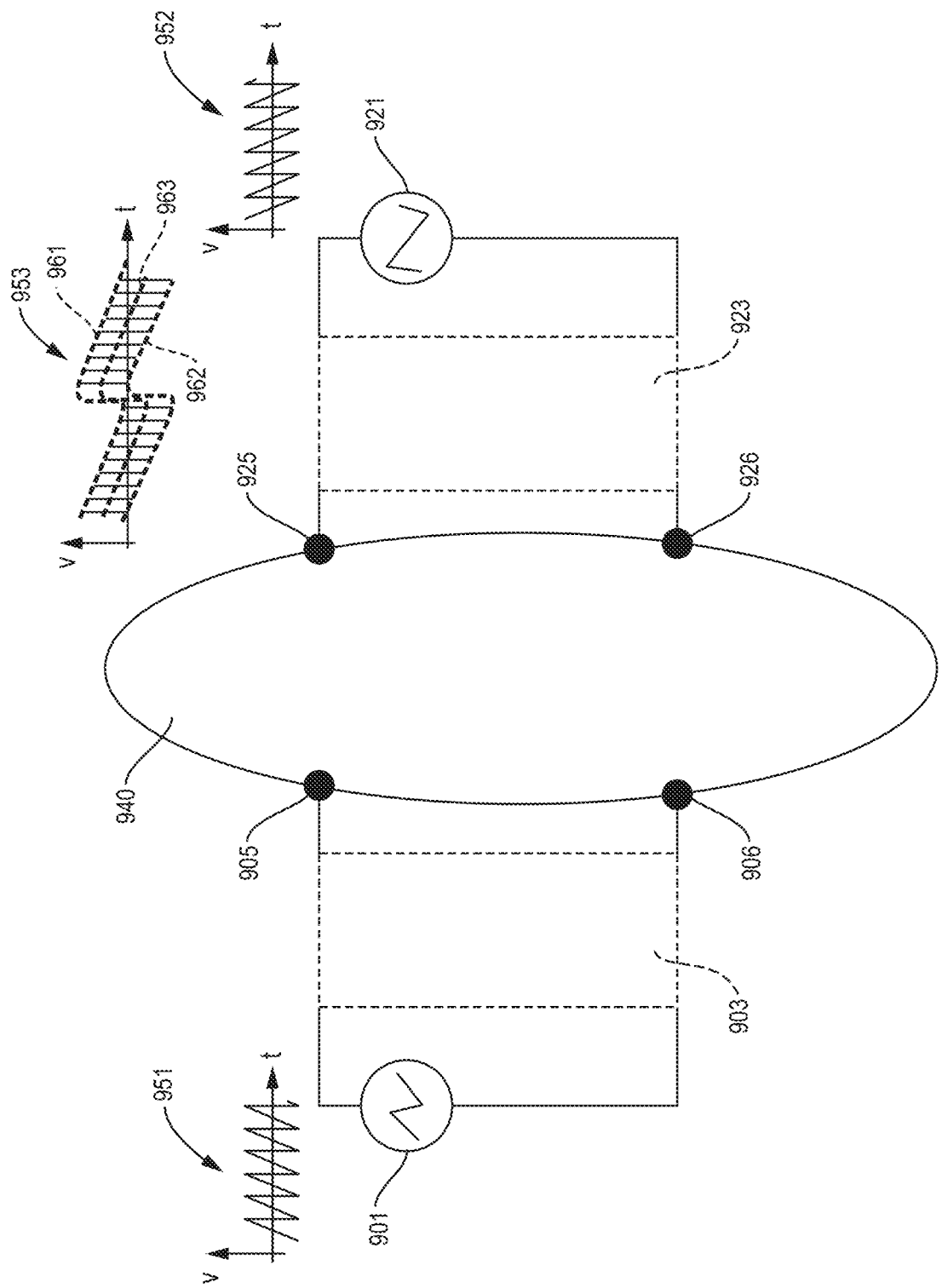

FIG. 9 shows a non-zero-mean envelope AM waveform formed by superposition of two temporally asymmetric waveforms.

Figure 10:
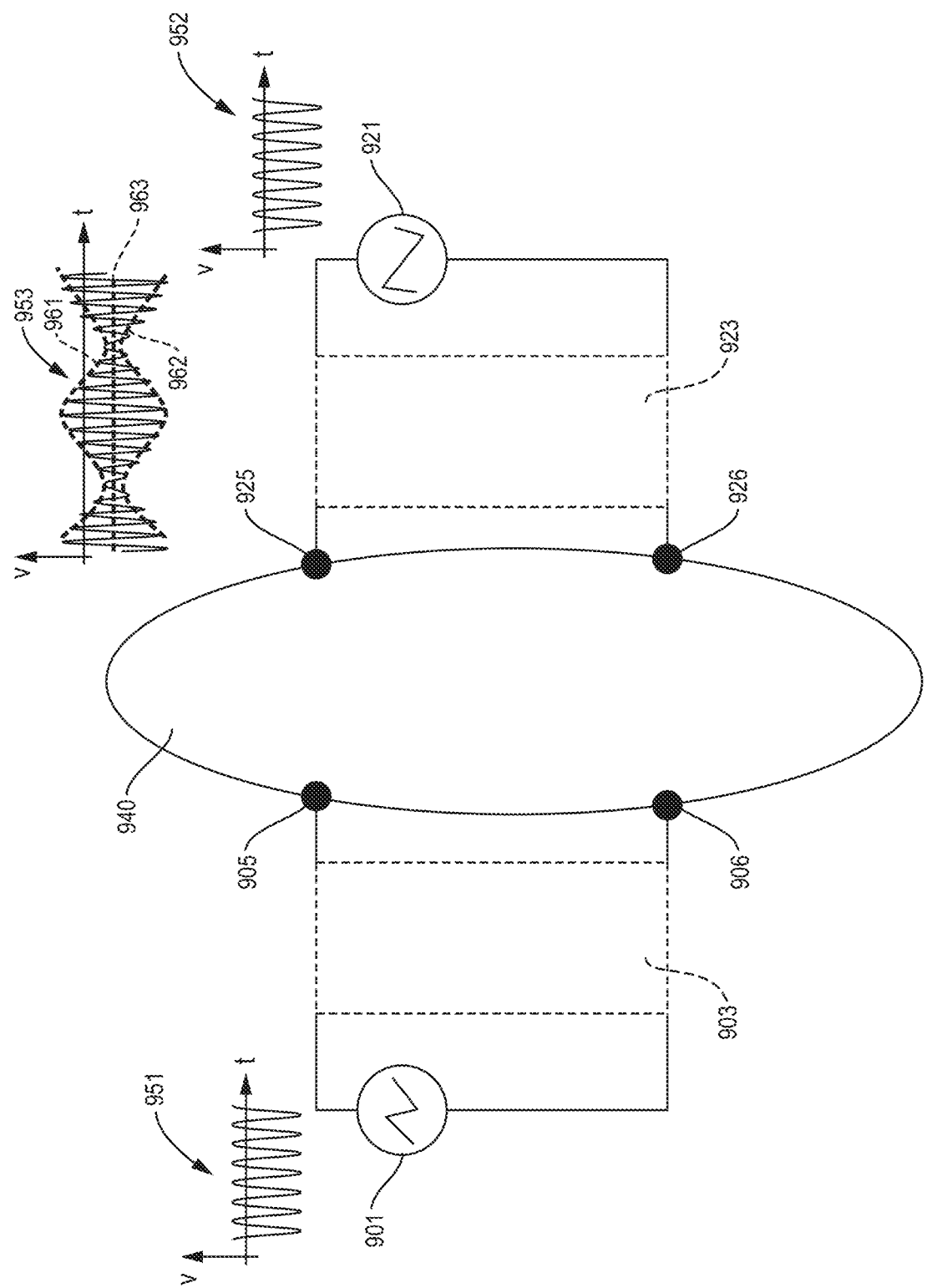

FIG. 10 shows a non-zero-mean envelope AM waveform formed by superposition of two waveforms that are amplitude offset from each other.

Figure 11:
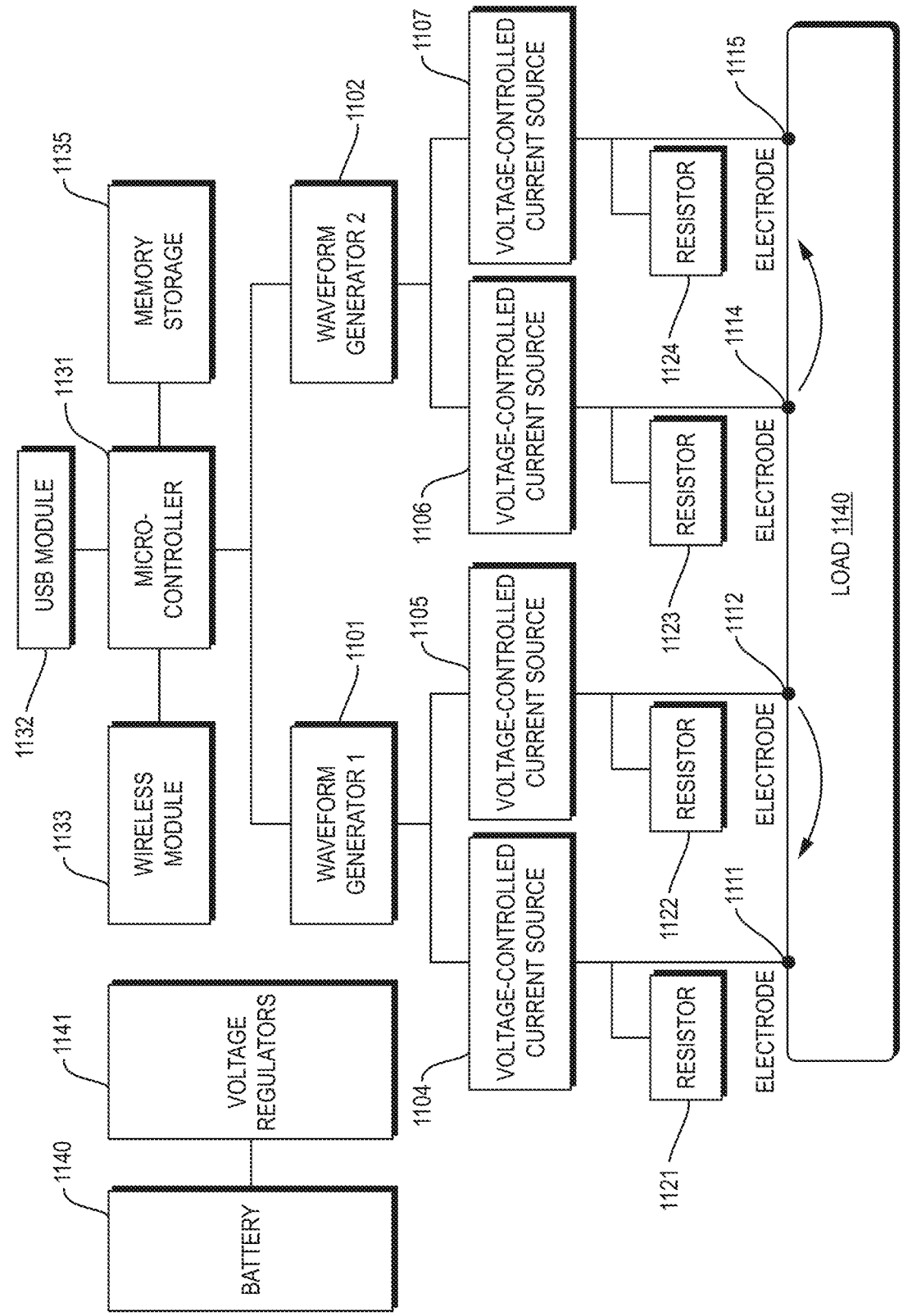

FIG. 11 shows hardware components of an anti-phasic current drive.

Figure 12:
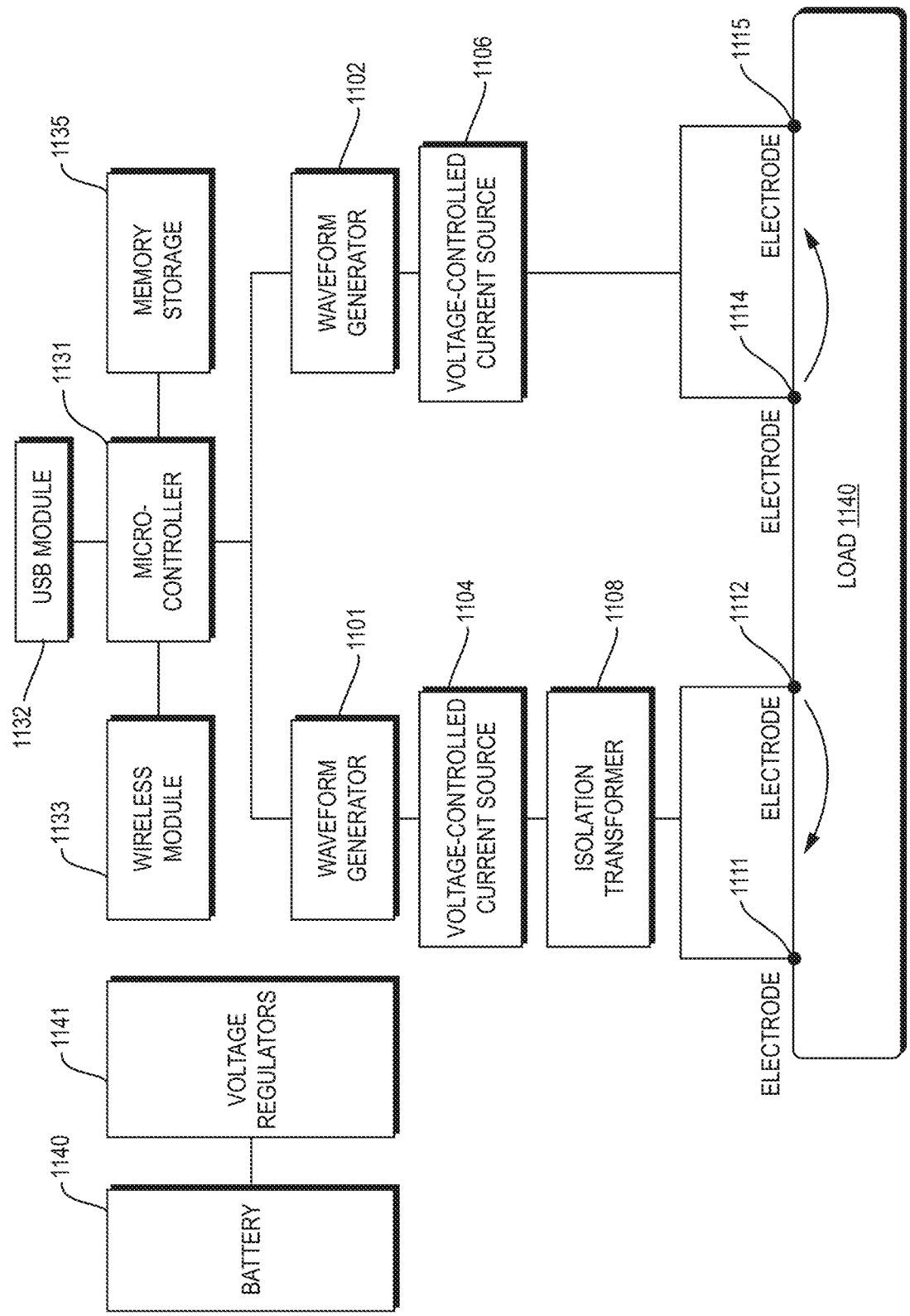

FIG. 12 shows hardware components of a current drive that includes an isolation transformer.

Figure 13:
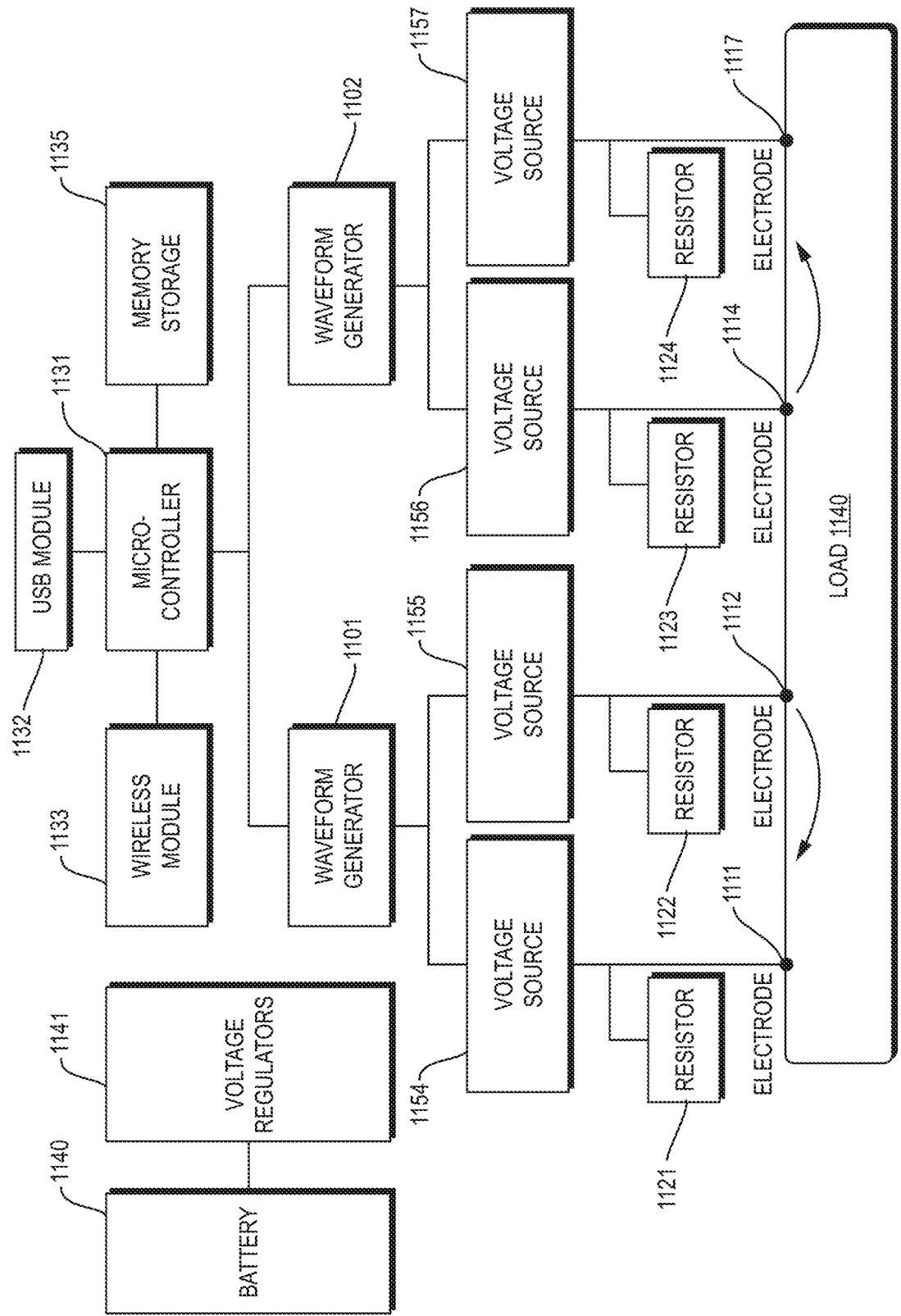

FIG. 13 shows hardware components of a voltage drive that is anti-phasic.

Figure 14:
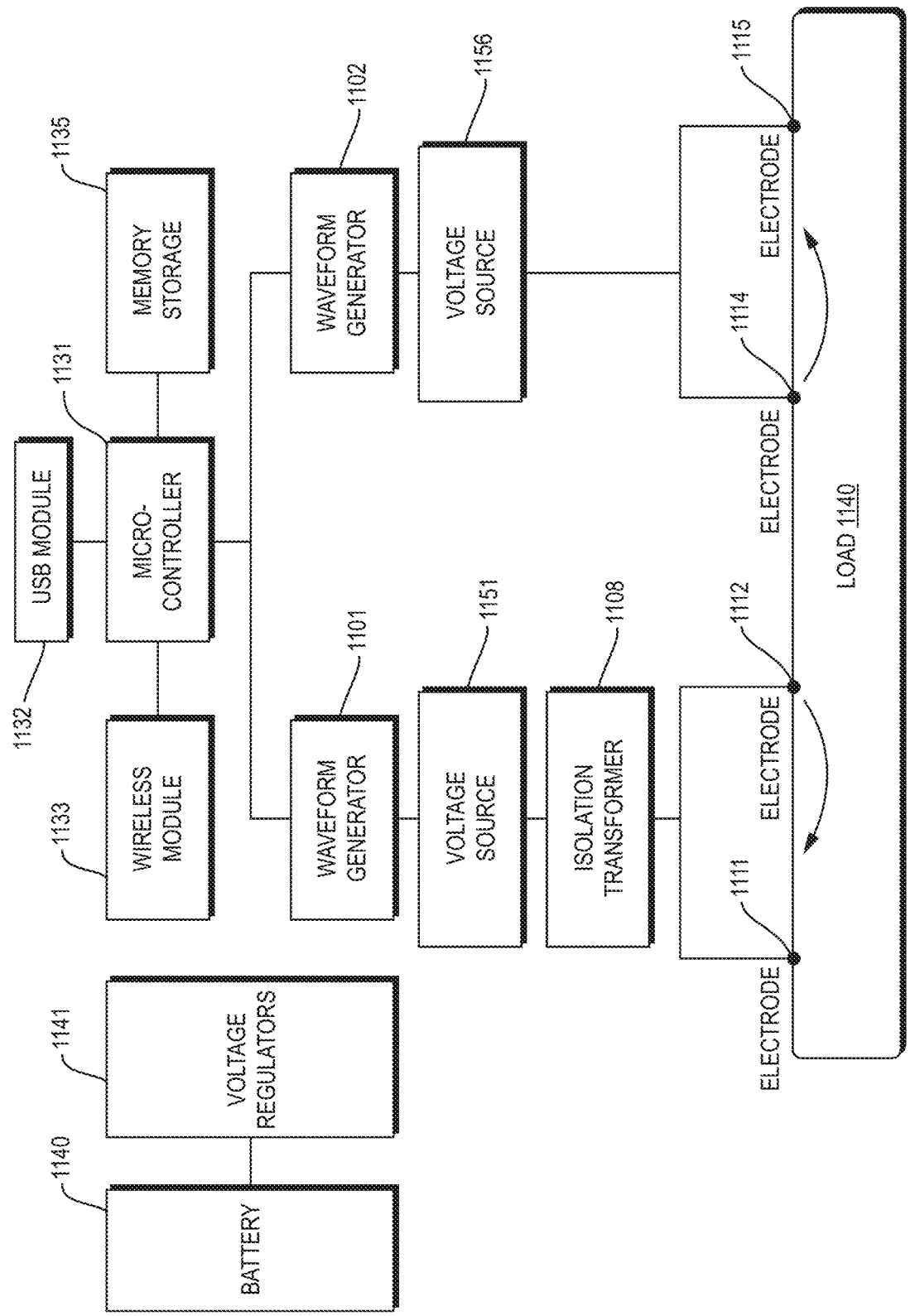

FIG. 14 shows hardware components of a voltage drive that includes a transformer.

FIGS. 15A, 15B, 15C, 15D, 15E and 15F show examples of electrodes positioned on neuromodulation targets.

FIGS. 1-2G, 4A-4D, 5B, 5F, 5G, 5K, 6C, 6H, 6I, 6L, 7, and 9-15E show illustrative implementations of this invention, or provide information that relates to those implementations. However, this invention may be implemented in many other ways.

DETAILED DESCRIPTION

Targeting Based on Envelope Amplitude

FIG. 1A is a conceptual diagram that illustrates envelope amplitude. In FIG. 1A, two current channels produce two original waveforms: channel 1 produces original waveform 111 and channel 2 produces original waveform 112. The amplitude of the first waveform 111 is $E_{ch1}$; and the amplitude of the second waveform 112 is $E_{ch2}$. The AM index is the ratio of these two amplitudes: AM index=$E_{ch1}/E_{ch2}$.

Interference of the two original waveforms 111, 112 produces an amplitude-modulated (AM) waveform 114. The AM waveform has an envelope 115. The top of the envelope is a signal. The peak amplitude of that signal is the envelope amplitude $E_{AM}$.

In illustrative embodiments of this invention, targeting is based on the envelope amplitude instead of the AM index. Specifically, in illustrative embodiments, targeting is based on controlling the spatial position of a region where the envelope amplitude is above a threshold or is at a maximum. This is different than conventional IFC, in which targeting attempts to control the spatial position of a region where the AM index is above a threshold or is at a maximum.

This distinction is important, because the region of maximum envelope amplitude does not necessarily coincide with the region of maximum interference, and is often quite different.

FIG. 1B illustrates an example in which the region of maximum interference does not overlap with the region of maximum envelope amplitude. In FIG. 1, a first current channel runs through a first pair of electrodes 121, 122. The second current channel runs through a second pair of electrodes 123, 124. The two pairs of electrodes are electrically connected to a common conductive load 125 (such as a brain). Arrows 126 and 127 represent the current from the first and second current channels, respectively, flowing in the conductive load 125. The arrows are merely symbolic—among other things, each current actually alternates in direction and flows through all regions of the conductive load.

In FIG. 1B, maximum envelope amplitude occurs in regions 128 and 129, but the region of maximum interference (where the electric field has the highest AM index) occurs at region 130.

FIGS. 1C and 1D show the envelope amplitude at two regions of FIG. 1B. Specifically, FIG. 1C shows the AM waveform 141 at region 128, and FIG. 1D shows the AM waveform 142 at region 130. The envelope amplitude is labeled $E_{AM}$.

The interference at region 130 is complete (modulation index is 100%) as shown in FIG. 1D. The interference at region 128 is less than complete (modulation index is less than 100%) as shown in FIG. 1C.

However, $E_{AM}$ (that is, the envelope amplitude) is greater at region 128 as shown in FIG. 1D, and is less at region 130 as shown in Figure AC.

Conventional IFC therapy would attempt to position region 130 at the target tissue, because region 130 has the maximum interference (modulation index=100%).

In contrast, an illustrative implementation of this invention would position region 128 or region 129 at the target tissue, because envelope amplitude is greatest in regions 128 and 129.

The size, shape and position of a region where the envelope amplitude exceeds a given threshold depends on the relative amplitudes of the two current channels and on the placement of the electrodes for the two channels. In illustrative embodiments of this invention, these factors are adjusted to precisely position this region at the targeted tissue. For example, in some use scenarios of this invention involving interferential stimulation, transcranial electrodes create electric fields in a brain such that: (i) an interferential zone is created close to one or more of the electrodes at a superficial depth in the brain (e.g. in the cortex); (ii) an interferential zone is created at a deeper depth of the brain but laterally close to the electrodes; or (iii) an interferential zone is created at any brain depth in a region that it is remote from the electrodes. In some cases, relative amplitude of the two original waveforms is used to control the size and location of an interferential zone in a brain.

In some embodiments of this invention, the first electrode pair and second electrode pair are positioned such that, at a given time, the largest magnitude of the envelope amplitude occurs in only one region of the brain. This region is path-connected and consists only of those points at which the largest magnitude of the envelope amplitude occurs. This region of highest envelope amplitude may be precisely targeted. For example, in some use cases of this invention, this region of highest envelope amplitude is positioned such that the region spatially coincides with (i) cortical tissue of a brain, (ii) subcortical tissue of a brain; (iii) heart tissue, or (iv) tissue in a nerve. More generally, in illustrative embodiments of this invention, this region of highest envelope amplitude is precisely positioned on target tissue anywhere in the body.

In some embodiments of this invention: (a) the amplitude modulated waveform has an envelope amplitude; (b) the greatest magnitude of the envelope amplitude occurs in a spatial position in the brain; (c) a volume exists, which volume consists of only those points at which the magnitude of the envelope amplitude is equal to at least 50% of the greatest magnitude; and (d) this volume coincides with both cortical and subcortical tissue of the brain.

Electrode Placement

In conventional IFC, the four stimulating electrodes are positioned in a crisscross pattern, in which each electrode is located at a corner of a rectangle (typically, a square). Thus, the line segment that joins the electrodes of one electrode pair is one diagonal of the rectangle, and the line segment that joins the electrodes of the other electrode pair is the other diagonal of the rectangle. These two diagonals cross each other, forming an X (crisscross) pattern. The electrodes are positioned so that the target tissue region is located at, or beneath, the center of the rectangle where the two crisscrossing diagonals intersect.

The electrode placement in FIG. 1B is an example of this conventional configuration. In FIG. 1B, the four electrodes 121, 122, 123, 124 are located at the four corners of a geometric rectangle 140. Arrows 126 and 127 coincide with the two diagonal lines that join opposite corners of the rectangle. In conventional IFC, the electrodes are positioned so that the target tissue is at, or beneath, the intersection of these two diagonals—that is, at or beneath position 130.

In contrast, electrode placement is more flexible, in illustrative embodiments of this invention.

Figure 1G:
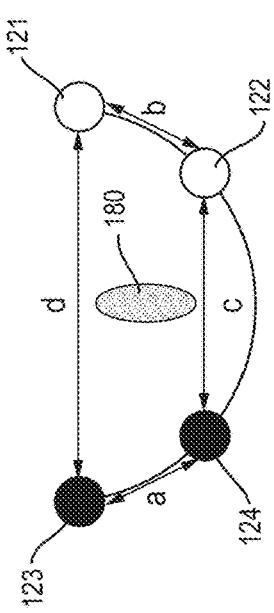
FIGS. 1E, 1F, 1G, 1H, 1I, 1J, 1K, and IL show examples of electrode configurations.
Figure 1J:
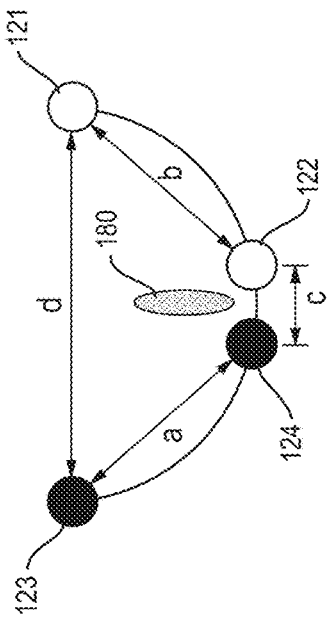
Figure 1F:
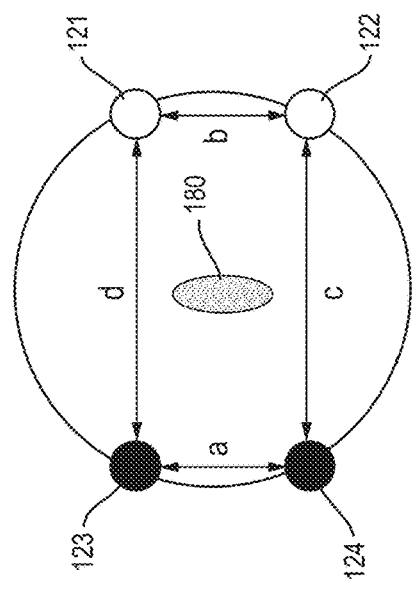
Figure 1I:
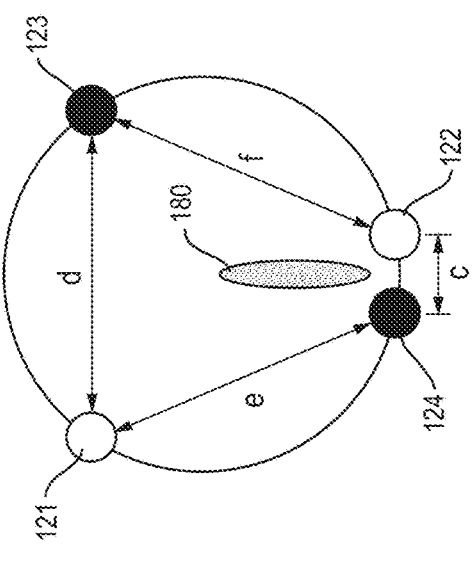
Figure 1E:
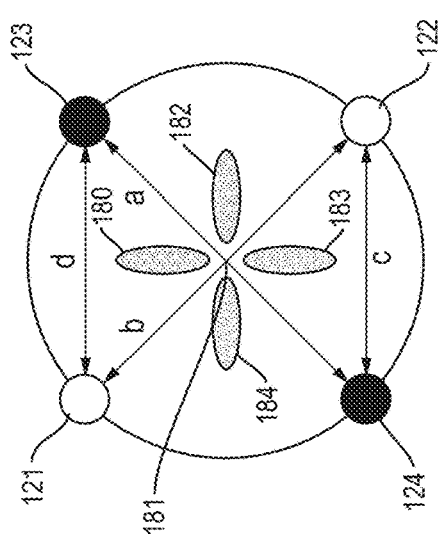

A rectangular configuration may be used with this invention (e.g., to target regions 128 or 129 in the example shown in FIG. 1B or to target regions 181, 182, 183, 184 in FIG. 1E). However, a rectangular configuration of stimulating electrodes is usually not desirable, for the reason discussed in the next paragraph, and so other electrode placements are typically used in illustrative embodiments of this invention.

FIGS. 1B and 1E illustrate a drawback of a conventional, crisscross configuration, in which two geometric line segments (one of which is between the electrodes in the first current channel and the other of which is between the electrodes in the second current channel) intersect or cross over each other. This drawback is that the crisscrossed electrodes produce multiple, separate regions (such as regions 128 and 129 in FIG. 1B, and regions 180, 182, 183, 184 in FIG. 1E) where the maximum envelope amplitude occurs. In typical use scenarios in which it is desired to provide interferential stimulation to only a single targeted location, the extra regions of maximum envelope amplitude are not desirable, since they stimulate at least one additional tissue region that is not an intended target. (Of course, if one is under the conventional misconception that the region of maximum interference—rather than the region of maximum envelope amplitude—should be positioned at the targeted tissue, this drawback is not apparent. The region of maximum interference typically occurs at the center of the conventional rectangular configuration where the crisscross intersects).

FIGS. 1F to 1L show examples of electrode configurations, in illustrative implementations of this invention. In the examples shown in FIGS. 1E to 1L, only one region 180 of maximum envelope amplitude occurs. This is advantageous, because in typical use scenarios, only one tissue is being targeted at a time, and thus it is advantageous to produce only one region of maximum envelope amplitude at time. The response of neurons (or other excitable cells) to the interferential stimulation is greatest where the envelope amplitude is greatest (at least, for amplitudes within the safe operating ranges of an interferential device treating a human).

A reason that only one region 180 of maximum envelope amplitude is produced in FIGS. 1F to 1L is that the pairs of electrodes are positioned side-by-side, rather than in a crisscross configuration. As used herein, a first pair of electrodes and a second pair of electrodes are positioned "side-by-side" if, for a first line segment that joins the electrodes of the first pair and a second line segment that joins the electrodes of the second pair, a geometric plane exists such that (i) the first line segment is positioned entirely on one side of the plane; (ii) the second line segment is positioned entirely on the other side of the plane; and (ii) neither the first line segment nor the second line segment intersect the plane. An example of a side-by-side configuration, showing such a geometric plane, is illustrated in FIG. 7.

In the examples FIGS. 1F to 1L, the electrode placement is unconventional, because the electrode pairs are positioned side-by-side, rather than in a crisscross pattern.

In FIGS. 1F to 1L, the gray region 180 is the region of greatest envelope amplitude. Electrodes 121 and 122 are the electrode pair for the first current channel. Electrodes 123 and 124 are the electrode pair for second current channel. Distance a is the distance between the two electrodes 123, 124 of the second electrode pair. Distance b is the distance between the two electrodes 121, 122 of the first electrode pair. Distance c is the distance between electrode 122 (in the first electrode pair) and electrode 124 (in the second electrode pair. Distance d is the distance between electrode 121 (in the first electrode pair) and electrode 123 (in the second electrode pair). Distance e is the distance between electrode 121 (in the first electrode pair) and electrode 124 (in the second electrode pair. Distance f is the distance between electrode 122 (in the first electrode pair) and electrode 123 (in the second electrode pair).

FIG. 1E shows an example of a conventional electrode configuration, which may be used in this invention. In FIG. 1E, the electrodes are at the four corners of a square, and the electrode pairs are arranged in a crisscross pattern. In FIG. 1E, four separate regions 180,182, 183, 184 of maximum envelope amplitude occur. This is usually disadvantageous, for the reasons discussed above.

FIGS. 1F to 1L show non-conventional electrode placements for interferential stimulation, which may be used in this invention.

In FIG. 1F, the electrodes are in a rectangular pattern, such that $a=b<c=d$.

Figure 1H:
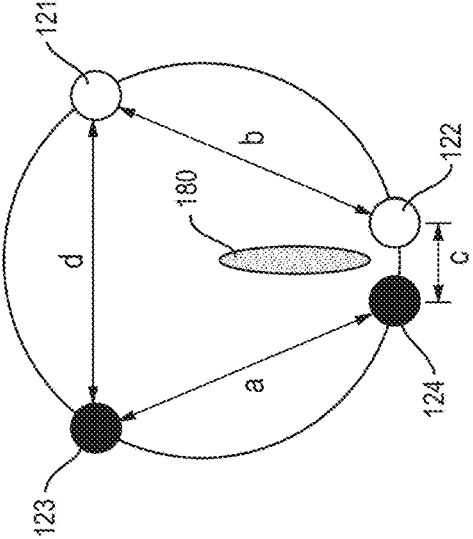

In FIGS. 1G to 1L, the electrodes are not positioned at the corners of a geometric rectangle. In FIG. 1G, $a=b<c<d$. In FIG. 1H, $c<d<a=b$. In FIG. 1I, $c<e=f<d$. In FIG. 1J, $c<a=b<d$.

Figure 1L:
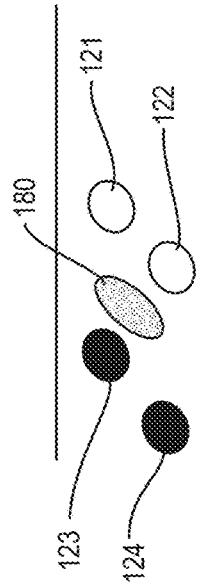
FIG. 1A is a conceptual diagram that illustrates envelope amplitude.
FIG. 1B illustrates an example in which the region of maximum interference does not overlap with the region of maximum envelope amplitude.
FIGS. 1C and 1D show the envelope amplitude at two regions of FIG. 1B.
FIG. 1M shows examples of geometric shapes along which electrodes may be positioned, in illustrative implementations of this invention.
Figure 1K:
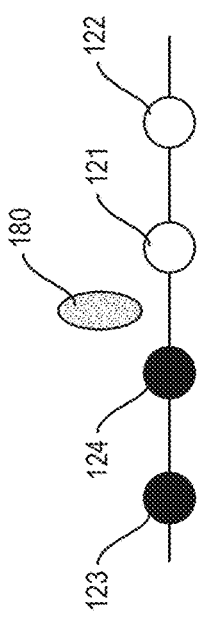

In FIG. 1K, the four electrodes 123, 124, 121, 122 are arranged in a straight line.

In FIG. 1L, the four electrodes 121, 122, 123, 124 are positioned at the corners (vertices) of a parallelogram that is not a rectangle.

Figure 1M:
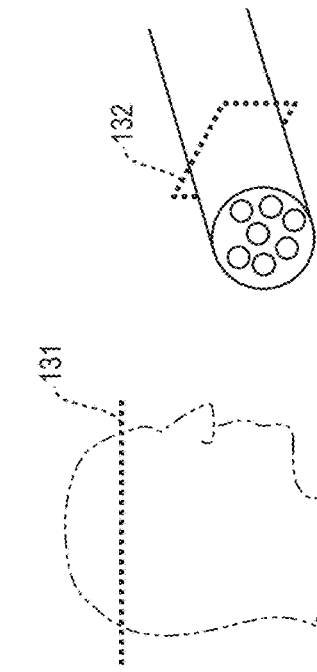

FIG. 1M shows examples of geometric shapes along which electrodes may be positioned, in illustrative implementations of this invention.

In some cases, the stimulating electrodes are arranged in a circle, semicircle, straight line or almost straight line. In some cases, all of the stimulating electrodes are positioned in a single plane, such as transverse plane 131, plane 132 (perpendicular to the longitudinal axis of a nerve), coronal plane 133, or sagittal plane 134. In some cases, the stimulating electrodes are placed in a straight line, as shown in FIG. 1K, or almost in a straight line. For example, in some case, the electrodes may be positioned on a slightly curved line segment 135 that touches, and conforms to the curvature of, the exterior of a head. In some cases, electrodes are positioned in a straight line along a probe that is inserted to a brain, such as electrodes 1525, 1526, 1527, 1528 which are disposed in a straight line near the tip of probe 1521, as shown in FIGS. 15C and 15D.

Modulation of Excitable Cells

In some implementations of this invention, an apparatus drives multiple electric currents through tissue comprising excitable cells in such a manner as to modulate activity of the tissue. In many cases: (a) the modulation occurs in spatial regions that are remote from the stimulating electrodes; and (b) the modulation is less pronounced or absent in regions closer to the stimulating electrodes. For example, the excitable cells may comprise neurons, and the modulated neural activity may comprise a neural spike train or neural oscillation. Or, for example, the excitable cells may comprise cardiomyoctes.

First, a few definitions:

"Threshold amplitude" for a given excitable cell means the minimum amplitude of a single electric field pulse that evokes an action potential in the given cell.

"Sub-threshold amplitude" for a given excitable cell means an amplitude that is less than the threshold amplitude for the given cell.

"Supra-threshold amplitude" for a given excitable cell means an amplitude that is greater than the threshold amplitude for the given cell.

To say that action potentials in a given excitable cell are "time-locked" with a sequence of peaks in an electrical waveform means that, for each respective peak in a sequence of peaks, an action potential occurs in the given cell after the respective peak and before the next peak if any in the sequence.

"Natural band" of a given excitable cell means a range of fundamental frequencies such that, for each respective fundamental frequency in the range, a sequence of supra-threshold peaks only at that respective fundamental frequency would evoke action potentials in the given cell that are timelocked with the sequence.

"Supra-threshold temporal summation" means a response by an excitable cell, wherein multiple sub-threshold peaks in temporal succession evoke an action potential in the cell.

In illustrative implementations, an apparatus drives two isolated currents through biological tissue, in such a manner as to evoke stable action potential oscillations in excitable cells. In some cases, in order to evoke these stable action potential oscillations, each of the two currents comprises a train of electrical field pulses with sub-threshold amplitude and a frequency higher than the cells' natural band. The two currents interfere with each other in such a manner as to produce an amplitude-modulated waveform. This AM waveform has a beat frequency that falls within the cells' natural frequency band and has a supra-threshold amplitude. The action potentials that are evoked are time-locked to the sequence of peaks of the AM waveform.

The following 14 paragraphs describe examples in which the excitable cells are neurons.

Electric fields may evoke action potentials or other modulation of neural activity.

A single pulse of electric field may evoke a single action potential. In this case the electric field pulse has supra-threshold amplitude. The threshold amplitude, i.e. minimum amplitude, to evoke an action potential is inversely dependent on the duration (or width) of the stimulating pulse. If the pulse durations are significantly longer than the time constant of the neuron (typically ~1 ms), a reduction in the pulse duration results in a small linear increase in the threshold. However, if the pulse durations are equal or smaller than the neuron time constant, a reduction in the pulse duration results in a large exponential increase in the threshold. This principle is known as the strength-duration response of neurons.

A train of electric field pulses, each with supra-threshold amplitude, may evoke a train of action potentials where each pulse evokes a time-locked action potential. In this case, the electric field peak amplitude needed to evoke a train of action potentials depends on the pulse duration and on the inter-pulse-interval since the neural membrane requires time to recover from an action potential event. (An incomplete recovery of the neural membrane potential results in a larger activation threshold).

If the electric field train is symmetrical or bio-phasic such as sinusoidal, i.e. the pulse width is equal to the inter-pulse-interval; the threshold to evoke a train of action potentials depends simply on the frequency of the electric field.

If the frequency of the electric field is sufficiently low, the interval after each electric field pulse is long enough to allow the neuron to sufficiently repolarize its membrane so the next electric field pulse can evoke a time-locked action potential.

In this frequency range (the neuron's natural frequency band), the rate of action potentials is directly proportional to the frequency of the electric field and the threshold to evoke a time-locked action potential oscillation is inversely proportional to the frequency of the electric field (higher frequency results in shorter pulse duration and shorter inter-pulse interval).

If the frequency of the electric field train is increased beyond the neuron's natural band, the neuronal membrane does not repolarize sufficiently between electric field pulses leading to the loss of the time-locked spiking. The actual rate of action potentials in this case may be significantly lower than the frequency of the electric field. Furthermore, if the electric field frequency is further increased eventually the neuron will remain depolarized to a level that suppresses any spiking activity.

A different response pattern emerges when the amplitude of the electric field pulse is lower than the threshold amplitude to evoke an action potential, i.e. sub-threshold. In this case, while a single pulse evokes only sub-threshold depolarization, if the inter-pulse interval is sufficiently small, a train of electric field pulses may be summed (or integrated) by the neuron to evoke supra-threshold, i.e. action potential, event. Thus, the neuron's response may comprise supra-threshold temporal summation, as defined herein. The amplitude that evokes a single action potential via supra-threshold temporal summation of sub-threshold pulses depends on the pulse duration and on the inter-pulse interval (the shorter the electric field inter-pulse interval the better it is summed up by the neuron). The efficiency of the temporal summation of the neuron is determined by its re-polarization rate, i.e. the rate by which the membrane returns to its rest potential value following an electrical stimulation.

If the electric field train is symmetrical or bio-phasic such as sinusoidal, the neural frequency response has a complex behavior as higher frequencies result in shorter pulse duration (i.e. higher threshold due to strength-duration response) but also shorter inter-pulse-interval (lower threshold due to stronger temporal summation). Overall, the frequency of the sub-threshold electric field must be larger than the natural frequency band to allow sufficient temporal summation.

A continuous train of sub-threshold electric field pulses may evoke a single action potential, via supra-threshold temporal summation, but typically does not evoke a stable time-locked train of action potentials as there is no stimulation free time for the neuron to repolarize after an action potential event. Typically, in this case, after the first action potentials, the neuron effectively stops to respond to the electric field and enters a steady-state in which its membrane is slightly depolarized above its rest potential and can respond to internal or external supra-threshold stimuli. (n some circumstances, there may be be a narrow amplitude-frequency range in which action potential oscillation occurs.)

The amplitude needed to evoke a train of action potentials at a certain natural frequency depends on the pulse duration (strength-duration response), the inter-pulse-interval (temporal summation) and on the strength of the amplitude modulation (the larger the reduction in the electric field amplitude, the stronger the repolarization of the neuron).

If the electric field train is symmetrical or bio-phasic such as sinusoidal, i.e. the pulse width is equal to the inter-pulse-interval, the threshold to evoke a train of action potentials at a certain natural frequency depends on the frequency of the electric field and the strength of the amplitude modulation.

Similar to the supra-threshold pulse train, the minimum amplitude of an AM waveform which will evoke an action potential oscillation that is timed-locked to the AM waveform is inversely proportional to the AM frequency of the electric field.

In the case of sub-threshold temporal summation, the neuron experiences periodic sub-threshold depolarization at a rate equal to the frequency of the amplitude modulation.

In illustrative implementations of this invention, an apparatus drives two isolated currents in order to cause stable action potential oscillations of neurons. These stable action potential oscillations are achieved by a train of electric field pulses with a sub-threshold amplitude and a frequency higher than the neurons' natural band (such that the inter-pulse interval is sufficiently small to achieve supra-threshold temporal summation). The two currents interfere with other to produce an amplitude-modulated waveform. The AM waveform has a frequency (sometimes called the beat frequency) in the neurons' natural band and has a supra-threshold amplitude. The AM waveform allows sufficient repolarization between action potentials. The AM waveform evokes a stable train of time-locked action potentials in the neurons.

The preceding 14 paragraphs describe examples in which the excitable cells are neurons. However, this invention is not limited to modulation of neurons. For example, in some cases, this invention modulates activity of cardiomyocytes or of other excitable cells.

When two alternating waves of different frequencies overlap, they create an alternating wave with an effective frequency that is equal to the average of the two original frequencies and an amplitude that changes periodically at a frequency that is equal to the difference of the original frequencies. The amplitude modulation (AM) is due to a periodic change between a constructive interference (when the two waves are nearly in phase) and a destructive interference (when the two waves are nearly 180 degrees out of phase). The frequency in which the amplitude changes is sometimes called a beat frequency, an amplitude modulation frequency, or an envelope frequency. The average of the two original frequencies is often called the carrier frequency. The creation of the amplitude modulation can be shown by using the trigonometry sum rule $$\sin\alpha + \sin\beta = 2\sin\left(\frac{\alpha+\beta}{2}\right)\cos\left(\frac{\alpha-\beta}{2}\right).$$

Consider the sum of a signal $y_1(t) = A \cdot \sin(2\pi f_1 t)$ and a signal $y_2(t) = A \cdot \sin(2\pi f_2 t)$, where $f_1 > f_2$. This sum is equal to $$y_{1+2}(t, r) = 2A \cdot \cos\left(2\pi\left(\frac{f_1 - f_2}{2}\right)t\right) \cdot \sin\left(2\pi\left(\frac{f_1 + f_2}{2}\right)t\right),$$

that is, a sine function at a frequency $$\frac{f_1 + f_2}{2}$$

with an amplitude 2A that changes periodically by a cosine function at a slow frequency of $$\frac{f_1 - f_2}{2}.$$

In some cases, application of two different frequencies to biological tissues such as the brain affects a larger variety of frequencies (e.g. harmonics) due to their nonlinear characteristics.

By spatially overlapping two electric fields, the amplitude of superimposed fields is modulated at a rate equal to the difference between the electric fields frequencies and at a strength equal to the difference between the electric field amplitudes. This principle is called "interferential summation" and the resulting AM frequency is sometimes called the "beat frequency". The location and spread of the AM field depends in part on the positioning of the stimulation electrodes relative to each other.

In illustrative implementations of this example, an apparatus drives two currents (such as a first alternating current produced by the first pair of electrodes 101, 104 and a second alternating current produced by the second pair of electrodes 102, 103) through a conductive biological medium in such a way as to eliminate or greatly reduce cross-talk between the two currents.

FIGS. 2A-2H show neural responses to a time-varying electric field, in illustrative implementations of this invention. The neural responses shown in FIGS. 2A-2H were evoked by a prototype of this invention, and occurred in anesthetized mice. In the example shown in FIGS. 2A-2H: (a) a first electrode was positioned 1.5 mm posterior from bregma and 1 mm right of midline; (b) a second electrode was positioned 1.5 mm posterior from bregma and 1.5 mm left of midline; and (c) a patch electrode was positioned 2.2 to 2.5 mm posterior to bregma and 0.5 mm left of midline.

Figure 2A:
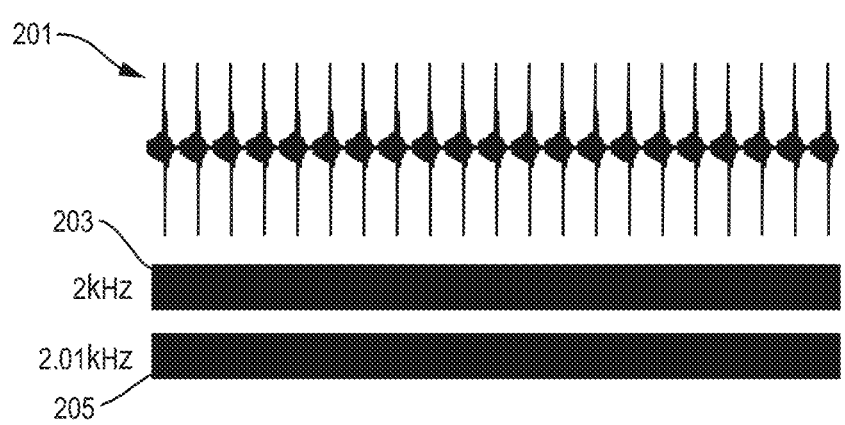
Figure 2B:
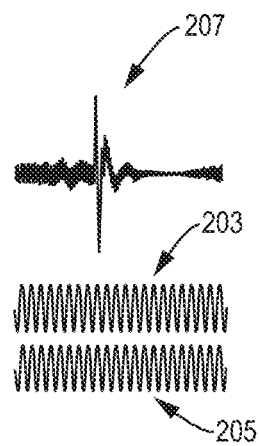

FIG. 2A shows a neural spike train 201 of a single neuron evoked by amplitude-modulated (AM) waveform formed by the intersection of a 2.00 kHz electrical field 203 and a 2.01 kHz electric field 205. FIG. 2B shows a zoomed view of a single action potential 207 in spike train 201 and a zoomed view of the 2.00 and 2.01 kHz electric fields 203, 205.

Figure 2C:
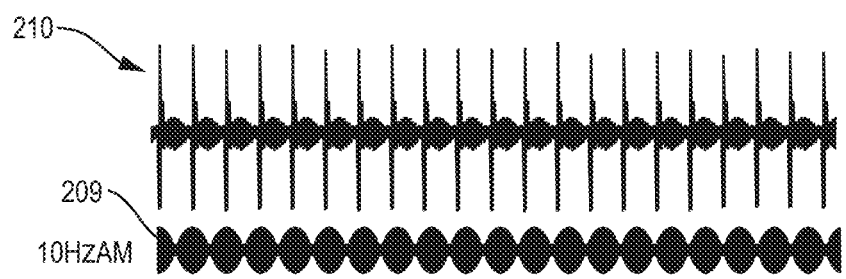
Figure 2D:
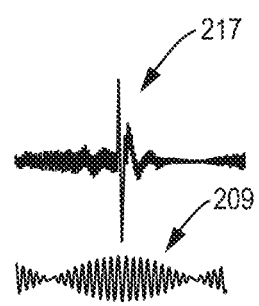

FIG. 2C shows a neural spike train 210 of a single neuron evoked by amplitude-modulated (AM) waveform 209 that has a 10 Hz beat frequency. FIG. 2D shows a zoomed view of a single action potential 217 in spike train 210 and a zoomed view of the AM waveform 209.

Figure 2E:
Figure 2F:
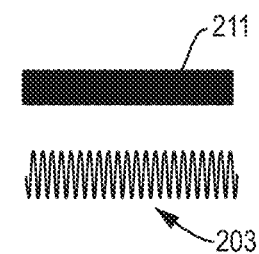

FIG. 2E shows a flat response 211 of a single neuron to stimulation by a single 2 kHz electric field 203. The response is flat in that the field does not evoke any action potential or other change in the neuron. FIG. 2F shows a zoomed view of the flat response 211 to the single 2 kHz electric field 203.

Figure 2G:
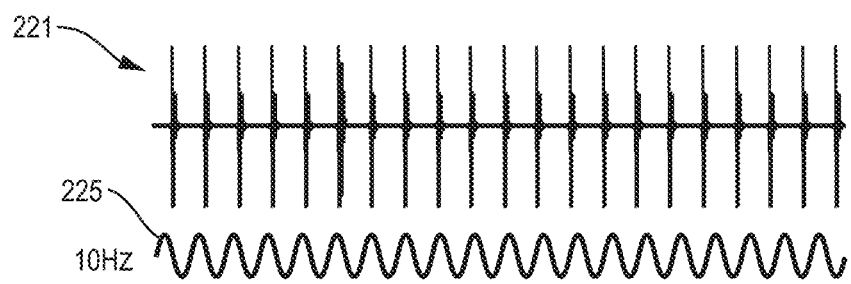
Figure 2H:
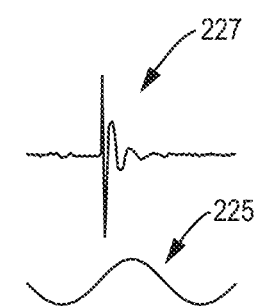

FIG. 2G shows a neural spike train 221 of a single neuron evoked by 10 Hz electric field 225. FIG. 2H shows a zoomed view of a single action potential 227 in spike train 221 and a zoomed view of the 10 Hz electric field 225.

In the examples shown in FIGS. 1A-1H: (a) a 2.00 kHz waveform does not evoke any action potential, (b) a 10 Hz electric field evokes a 10 Hz neural spike train; and (c) an AM waveform that is formed by the intersection of 2.00 kHz and 2.01 kHz electric fields and that has a beat frequency of 10 Hz evokes a 10 Hz neural spike train.

In FIGS. 2B, 2D, 2F, and 2H, the zoomed views are horizontally (temporally) zoomed.

In some implementations of this invention, electric fields are applied via electrodes. In some other implementations, an electric field is generated from an inductive source (e.g. coil) using time-varying magnetic field.

In some cases, the current sources produce an electric field pulse. The pulse may have different shapes (e.g. rectangular, sine, Gaussian, etc.)

In use scenarios that evoke an electric field pulse train, the train may be of any polarity (e.g. uni-phasic or bi-phasic), symmetrical or asymmetrical. It can also be sinusoidal.

Isolated Currents

Thus, in conventional current drive techniques, the amplitude modulation (AM) of the electric field is not well localized in a tissue (or any conductive medium) due to crosstalk between the current waveforms. In conventional current drive techniques, current from one channel is diverted toward the return path of the second channel leading to a strong amplitude modulation at the electrodes themselves. In the case of conventional interferential stimulation, this may result in the appearance of a beat frequency near the electrodes and not inside the tissue.

In illustrative implementations of this invention, this problem (of current leakage) is solved by using a current drive that is anti-phasic or that includes an isolation transformer. The current drive isolates the two currents so that current leakage between the two channels is greatly ameliorated.

In the case of interferential stimulation, this invention enhances the penetration and localization of an interferential stimulation into deep tissue layers.

More generally, this invention may be beneficial in any circumstance in which more than one electric waveform is applied to a conductive medium. In some cases, an isolated current drive provides isolated and localized stimulation of two or more areas of a tissue. For example, in some use scenarios, one segment of a neural tissue is stimulated with one waveform (e.g. 10 Hz) and another nearby segment of the same neural tissue is stimulated with the same or different waveform (e.g. 20 Hz or DC) without interference currents. The neural segments may be a few micrometers or millimeters apart as in the case of an invasive stimulator with multiple electrodes or a few centimeters apart as in the case of noninvasive stimulator.

In illustrative implementations of this invention, an isolated current drive is implemented either with an anti-phasic source or with an isolation transformer.

Anti-phasic Source: In the anti-phasic case, a current source drives two different electric waveforms through balanced pairs of electrodes, one waveform through a first pair of electrodes and a second waveform through a second pair of electrodes. At least one electrode pair is anti-phasic, that is, the phase at the first electrode of the pair is substantially anti-phasic (substantially 180 degrees out-of-phase) from the phase at the second electrode of the pair. In some cases, only one of the electrode pairs is anti-phasic. In other cases, both of the two electrode pairs is anti-phasic. In some cases, a ground or reference electrode is provided to carry any imbalance currents from the paired currents sources and to prevent charge up of the body relative to earth ground. The vast majority (>99%) of the stimulation current created by each electrode pair does not flow through this ground or reference electrode since the current is driven differentially or out of phase with each other. A benefit of this approach is that most of the current is not going through the common ground electrodes. This allows multiple current waveforms to flow independently inside the tissue. This eliminates (or greatly reduces) crosstalk between the channels and permits triangulation of the currents through the conductive medium away from the path of current to the ground.

Isolation Transformer: In the isolation transformer case, two current waveforms are isolated from each other by connecting the primary wires of a transformer to a single current source and a ground and connecting the floating secondary wires of the transformer to two or more stimulating electrodes. This configuration greatly reduces crosstalk between the two channels, and thus has a similar effect as an anti-phasic drive. In some cases, a ground or reference electrode is provided to prevent charge up of the body due to static electrical sources from the environment. In some cases, a conventional current source with a ground return electrode creates one stimulus waveform and all other electrodes are isolated by transformers.

Thus, in illustrative implementations of this invention, the two currents are isolated from each other, even though the currents are flowing simultaneously through a single conductive medium. This improves the efficiency of the modulation of excitable cells (e.g., neurons).

The discussion above refers to electric field but it is valid as well to electric current or electric potential.

The discussion above refers to a single action potential but it is valid also to a burst of action potentials.

The discussion above to neural cells however it is valid as well to other excitable cells such as muscle cells such as cardiomyocytes and to nerves such as the vestibular nerve.

FIG. 3 shows a conventional IFC device that applies multiple currents to a common conductive load (the load comprises a portion of the body). In FIG. 3, two waveform generators 301, 321 generate voltage waveforms that control voltage-controlled current sources 302, 322. A first electrode pair 305, 306 and a second electrode pair 325, 326 are each electrically attached to a common conductive load 340. Current source 302 drives a first current, and current source 322 drives a second current. The return pathway of each current source is connected to ground. In this conventional configuration, there is substantial current leakage between the first and second currents.

(In FIG. 3, nodes at which electrical wires connect are indicated by a dot. However, this convention is not followed in any other Figure. For example, in FIGS. 4A, 4B, 4C, 4D, 8, 9, and 10, nodes at which electrical wires connect are not indicated by a dot.)

FIGS. 4A, 4B and 4C each show examples of an anti-phasic current drive for applying isolated currents to a common conductive load, in illustrative embodiments of this invention. For example, the common conductive load 440 may comprise biological tissue such as a brain or head.

In FIGS. 4A, 4B, and 4C, a left-side electrical network comprises (a) a first pair of electrodes 405, 406 and (b) the circuit components positioned to the left (in these Figures) of this first pair of electrodes. In FIGS. 4A, 4B, and 4C, a right-side electrical network comprises (a) a second pair of electrodes 425, 426 and (b) circuit components positioned to the right (in these Figures) of this second pair of electrodes.

In FIGS. 4A, 4B and 4C, the right-side network is anti-phasic—that is, the right-side network creates electrical waveforms in an electrode pair (a first waveform at electrode 405 and a second waveform at electrode 406), such that these two waveforms have a phase difference that is substantially equal to 180 degrees.

In FIGS. 4B and 4C, the left-side network is also anti-phasic—that is, the left-side network creates electrical waveforms in an electrode pair (a first waveform at electrode 425 and a second waveform at electrode 426), such that these two waveforms have a phase difference that is substantially equal to 180 degrees.

In FIGS. 4A, 4B and 4C, two waveform generators 401, 421 generate voltage waveforms that control voltage-controlled current sources (i.e., current sources 402, 403, 422 in FIG. 4A, and current sources 402, 403, 422, 423 in FIG. 4B).

In FIGS. 4A, 4B and 4C, waveform generator 401 generates a voltage waveform that: (a) is converted to an in-phase current waveform by voltage-controlled current source 402 and applied to a common conductive load 440 via electrode 405; and (b) is converted into an anti-phase current waveform by a voltage-controlled current source 406 and applied to the load 440 via electrode 406. Electrodes 405 and 406 have a phase difference that is substantially equal to 180 degrees. This phase difference is achieved by connecting waveform generator 401 to the positive input of voltage-controlled current source 402 and to the negative input of a second voltage-controlled current source 403.

In FIG. 4A, waveform generator 421 generates a voltage waveform that is converted to a current waveform by voltage-controlled current source 422 and applied to the common conductive load 440 via a pair of electrodes 425, 426.

In FIGS. 4B and 4C, waveform generator 421 generates a voltage waveform that: (a) is converted to an in-phase current waveform by voltage-controlled current source 422 and applied to the common conductive load 440 via electrode 425; and (b) is converted into an anti-phase current waveform by a voltage-controlled current source 426 and applied to the load 440 via electrode 426. In FIGS. 4B and 4C, electrodes 425 and 426 have a phase difference that is substantially equal to 180 degrees. This phase difference is achieved by connecting waveform generator 421 to the positive input of voltage-controlled current source 422 and to the negative input of a second voltage-controlled current source 423.

In FIG. 4B, a reference electrode 407 is connected to ground 404. The reference electrode 407 carries any imbalance currents from the paired currents sources and prevents charge up of the load 440 relative to earth ground.

In FIG. 4C, the reference electrode 407 is replaced with four resistors 408, 409, 428, 429. Each of these resistors, respectively, shares a node with one of the electrodes (405, 406, 425 or 426) at one end of the resistor and is electrically connected to ground at another end of the resistor. The resistors carry any imbalance currents from the paired currents sources and prevent charge up of the load relative to earth ground.

The impedance of each of these resistors is preferably at least 10-fold larger than the impedance of the load 440, in order to limit the current flow to ground. A variable resistor may be used to adjust the resistance according to the load.

Four resistors 408, 409, 428, 429 are shown in FIG. 4C. However, in some cases, less than four of these resistors are employed. For example, one, two or three of these resistors may be included in the current drive apparatus, in order to carry any imbalance currents from the paired currents sources and to prevent charge up of the load 440 relative to earth ground.

Thus, FIGS. 4A, 4B and 4C all show examples of "anti-phasic" current drive.

It is worth noting that a prior art technology is sometimes called "anti-phasic", even though its structure and function is quite different. As is well known, the position and size of an interferential region may be adjusted, by adjusting the relative amplitudes of the original waveforms. Steering the position of the interferential region in this way is sometimes called "vector rotation", because it changes the position vector of the interferential region. In some prior art: (a) the amplitude of one of the original waveforms is increased while the amplitude of the other original waveform is simultaneously decreased, and (b) such reciprocal, simultaneous vector rotation is sometimes called anti-phasic. However, so-called anti-phasic vector rotation is quite different than an anti-phasic current drive of the present invention. Among other things, the vector rotation does not involve applying current to a load via a pair of electrodes that are in electrical antiphase to each other.

FIG. 4D shows an example of a current drive that includes an isolation transformer, and that is configured to apply isolated currents to a common conductive load, in an illustrative embodiment of this invention. In FIG. 4D, a waveform generator 401 generates a voltage waveform that is converted to a current waveform by voltage-controlled current source 402 and applied to a common conductive load 440 via a pair of electrodes 405, 406 through an isolation transformer 451. In this case the primary wires 454, 455 of transformer 451 are connected to the output of the current source and to a ground and the floating secondary wires 452, 453 of the transformer 451 are connected to electrodes 405, 406.

In FIG. 4D, waveform generator 421 generates another voltage waveform that is converted to a current waveform by voltage-controlled current source 422. The current is applied to the common conductive load 440 via a pair of electrodes 425, 426.

More Details

FIGS. 5A, 5B, 5C, 5D, 5E, 5F, 5G, 5H, 5I, 6A, 6B, 6C, 6D, 6E, 6F, 6G, 6H, and 6I show measured values of electrical fields in a 2D phantom. The phantom comprised Ag wire electrodes (1 mm cross-section) mounted in a Petri dish with a radius R of 25 mm. The Petri dish was filled with 0.9% saline solution. Measurements were taken with two orthogonal dipoles contracted from stainless-steel needle electrodes.

Figure 5A:
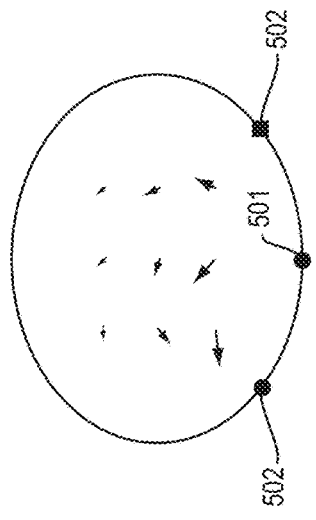
Figure 5B:
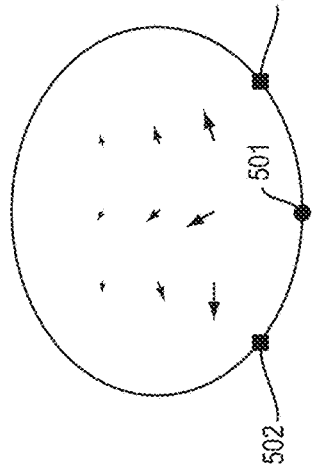
Figure 5C:
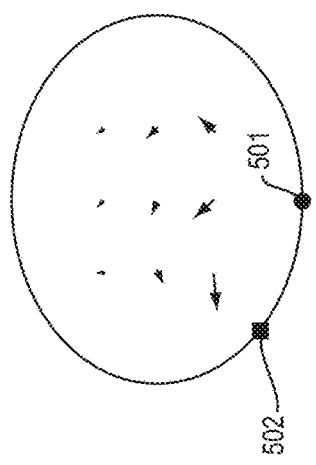
Figure 5D:
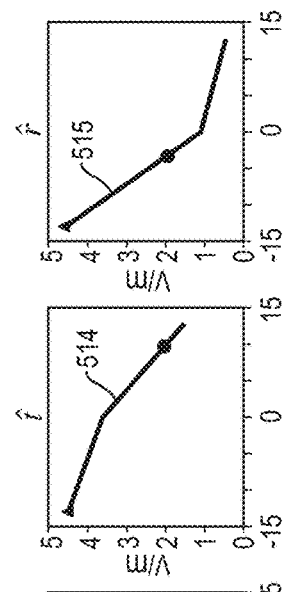
Figure 5E:
Figure 5F:
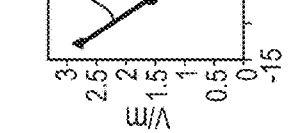
Figure 5G:
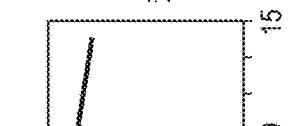
Figure 5H:
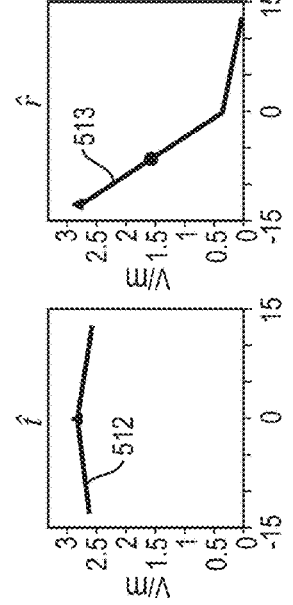
Figure 5I:
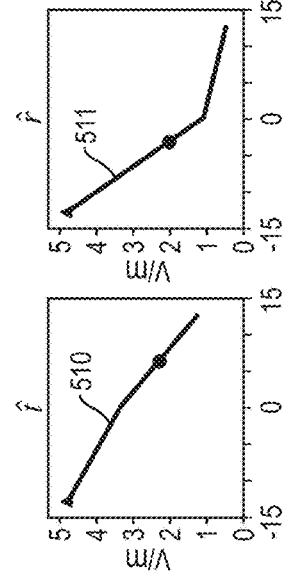
Figure 5J:
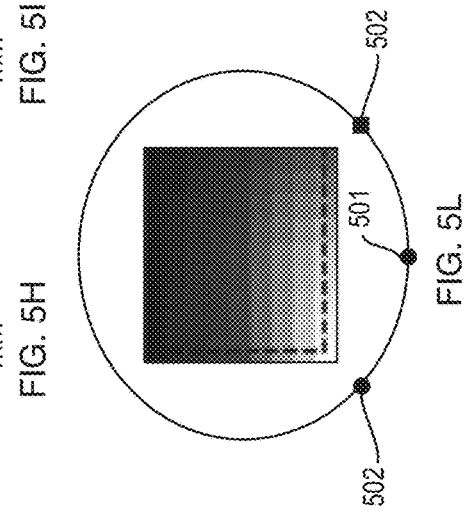

FIG. 5J shows a 2D grayscale amplitude map of a first electrical field created by passing current between electrode 501 and ground electrode 502. FIG. 5A shows a vector map of this first field. FIG. 5D shows a 1D amplitude distribution 510 of this first field along a tangential ($\hat{t}$) orientation. FIG. 5E shows a 1D amplitude distribution 511 of this first field along a radial ($\hat{r}$) orientation.

Figure 5K:
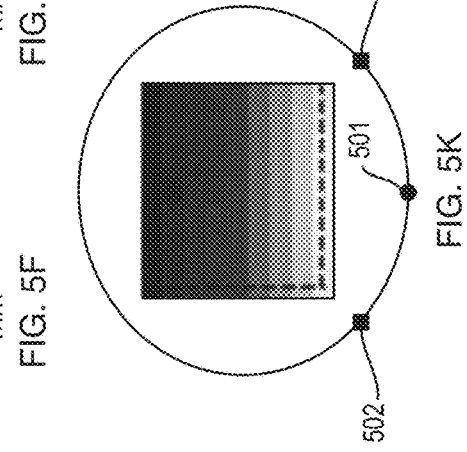

FIG. 5K shows a 2D grayscale amplitude map of a second electrical field created by passing current between electrode 501 and two ground electrodes 502. FIG. 5B shows a vector map of this second field. FIG. 5F shows a 1D amplitude distribution 512 of this second field along a tangential ($\hat{t}$) orientation. FIG. 5G shows a 1D amplitude distribution 513 of this second field along a radial ($\hat{r}$) orientation.

In the example shown in FIG. 5K (and in FIGS. 5B, 5F and 5G), an isolated current drive is not employed. As a result, there is major current leakage.

Figure 5L:
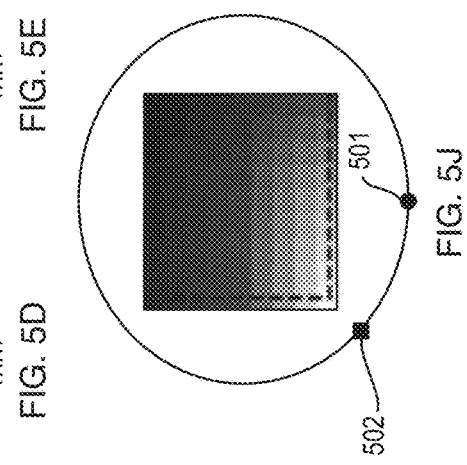

FIG. 5L shows a 2D grayscale amplitude map of a third electrical field created by passing current between electrode 501 and two ground electrodes 502. FIG. 5C shows a vector map of this third field. FIG. 5H shows a 1D amplitude distribution 514 of this third field along a tangential ($\hat{t}$) orientation. FIG. 5I shows a 1D amplitude distribution 515 of this third field along a radial ($\hat{r}$) orientation.

In the example shown in FIG. 5L (and in FIGS. 5C, 5H and 5I), an anti-phasic current drive is employed. As a result, current leakage is greatly ameliorated, causing the amplitude distribution and vector maps of the third field to look very similar those of the first field.

In FIGS. 5D, 5E, 5F, 5G, 5H and 5I, the FWHM (full width half maximum of electric field distribution) is equal to 0.75 R, 0.2 R, >R, 0.25 R, 0.9 R and 0.2 R, respectively, where R is the radius of the Petri dish.

FIG. 6J shows a 2D grayscale amplitude map of a fourth electrical field created by passing current between electrode 601 and ground electrode 605. FIG. 6A shows a vector map of this fourth field. FIG. 6D shows a 1D amplitude distribution 610 of this fourth field along a tangential ($\hat{t}$) orientation. FIG. 6E shows a 1D amplitude distribution 611 of this fourth field along a radial ($\hat{r}$) orientation.

FIG. 6K shows a 2D grayscale amplitude map of a fifth electrical field created by passing a first current with a kHz frequency between electrodes 601 and 602 and passing a second current with a different kHz frequency between electrodes 603 and 604. FIG. 6B shows a vector map of this fifth field. FIG. 6F shows a 1D amplitude distribution 612 of this fifth field along a tangential ($\hat{t}$) orientation. FIG. 6G shows a 1D amplitude distribution 613 of this fifth field along a radial ($\hat{r}$) orientation.

In the example shown in FIG. 6K (and in FIGS. 6B, 6F and 6G), an anti-phasic current drive is employed. As a result, current leakage is greatly reduced, causing the amplitude distribution and vector maps of the fifth field to look very similar those of the fourth field.

FIG. 6L shows a 2D grayscale amplitude map of a sixth electrical field created by passing a first current with a first between electrode 601 and ground electrode 608 and a second current with a different kHz frequency between electrode 603 and ground electrode 609. FIG. 6C shows a vector map of this sixth field. FIG. 6H shows a 1D amplitude distribution 614 of this sixth field along a tangential ($\hat{t}$) orientation. FIG. 6I shows a 1D amplitude distribution 616 of this sixth field along a radial ($\hat{r}$) orientation.

In the example shown in FIG. 6L (and in FIGS. 6C, 6H and 6I), an anti-phasic current drive is not employed. As a result, a large amount of current leakage occurs, and the sixth field looks very different than the fourth field.

In FIGS. 6D, 6E, 6F, 6G, 6H and 6, the FWHM (full width half maximum of electric field distribution) is equal to 0.5 R, 0.5 R, 0.5 R, R, R and 0.6 R, respectively, where R is the radius of the Petri dish.

In some implementations of this invention, it is desirable to position electrodes in a side-by-side configuration, rather than a crisscross configuration. FIG. 7 shows an example of side-by-side positioning of electrode pairs. In FIG. 7, a first pair of electrodes 702, 703 is positioned on a scalp of a human head, such that the first pair of electrodes is side-by-side with a second pair of electrodes 705, 706. Line segment 701 is between the electrodes of the first pair (i.e., the endpoints of line segment 701 are at electrodes 702 and 703, respectively). Line segment 704 is between the electrodes of the second pair (i.e., the endpoints of line segment 704 are at electrodes 705 and 706, respectively). The two line segments 701, 704 do not intersect each other and do not intersect plane 722. Line segment 701 lies entirely on one side of plane 722, and line segment 704 lies entirely on the other side of plane 722.)

In some implementations of this invention, the shape of the AM waveform is modified in order to improve the efficiency by which AM electric fields modulate neural activity. By creating AM electric fields with non-zero average envelop via a temporal asymmetry or amplitude offset, action potentials may be evoked with lower threshold amplitude.

FIG. 8 shows a conventional zero-mean envelope AM electric field. In FIG. 8, an AM electric field has a zero mean envelope (the sum of instantaneous positive and negative envelopes is zero. The AM field 853 is formed inside a conductive load 840 by superposition of two zero-mean sinusoidal electric waveforms 851, 852 that are generated by waveform generators 801, 802. In FIG. 8, waveform generators 801, 802 output voltage waveforms that converted to current waveforms via voltage-controlled current sources 803, 823, respectively. The current waveforms are applied to conductive load 840 via electrodes 805, 806, 825, 826. The instantaneous mean envelope 863 is zero and is equal to the instantaneous mean of the top of envelope 861 and the bottom of envelope 862.

FIG. 9 shows a non-zero-mean envelope AM waveform formed by superposition of two temporally asymmetric waveforms, in an illustrative implementation of this invention. In FIG. 9, an AM electric field has a non-zero mean envelope. The AM field 953 is formed inside a conductive load 940 by superposition of a first sawtooth waveform with slow rise and fast fall and a second sawtooth waveform with a fast rise and a slow fall. The first and second sawtooth waveforms are voltage waveforms that are generated by waveform generators 901, 921 respectively. In FIG. 9, the amplitude-modulated waveform has an envelope that has a top and a bottom. The difference between the voltage at the top and the voltage at the bottom is not equal to zero during at least part of the amplitude-modulated waveform.

FIG. 10 shows a non-zero-mean envelope AM waveform formed by superposition of two waveforms that are amplitude offset from each other, in an illustrative implementation of this invention. In FIG. 10, an AM electric field has a non-zero mean envelop. The AM field 953 is formed inside a conductive load by superposition of two sinusoidal electric waveforms 951, 952 with amplitude offset. In some cases, the amplitude offset may be due to D.C. biasing. FIG. 10 shows that both original waveforms 951 and 952 are amplitude offset. Alternatively, in some cases, the only one of original waveforms 951, 952 is amplitude offset. In FIG. 10, the first and second electrical fields are periodic. For each of these fields, the integral of the voltage of the field, over an entire period of the field, is equal to zero relative to earth ground.

In both FIGS. 9 and 10, the waveform generators output voltage waveforms that are converted to current waveforms via voltage-controlled current sources 903, 923 respectively. The current waveforms are applied to conductive load 940 via electrodes 905, 906, 925, 926. The instantaneous mean envelope 963 is non-zero at most points and is equal to the instantaneous mean of the top of envelope 961 and the bottom of envelope 962.

The schematics in FIGS. 4A-4D and 8-10 are conceptual and simplified and, in many cases, do not show all of the components of the electrical network. For example, the network may include switches, amplifiers, and other hardware not shown in the schematics.

FIG. 11 shows hardware components of an anti-phasic current drive. In FIG. 11, waveform generator 1101 outputs a voltage waveform that controls voltage-controlled current sources 1104, 1105, that in turn apply a current to conductive load 1140 via electrodes 1111, 1112. Likewise, waveform generator 1102 outputs a voltage waveform that controls voltage-controlled current sources 1106, 1107, that in turn apply current to conductive load 1140 via electrodes 1114, 1115.

FIG. 12 shows hardware components of a current drive that includes an isolation transformer. In FIG. 12, waveform generator 1101 outputs a voltage waveform that controls voltage-controlled current source 1104, that in turn applies a current to the primary wires of an isolation transformer 1108. Secondary wires of the transformer apply current to conductive load 1140 via electrodes 1111, 1112. Waveform generator 1102 outputs a voltage waveform that controls voltage-controlled current source 1106, that in turn applies current to conductive load 1140 via electrodes 1114, 1115.

FIG. 13 shows hardware components of a voltage drive that is anti-phasic. In FIG. 13, waveform generator 1101 outputs a voltage waveform that controls voltage-controlled voltage sources 1154, 1155, that in turn apply a current to conductive load 1140 via electrodes 1111, 1112. Likewise, waveform generator 1102 outputs a voltage waveform that controls voltage-controlled voltage sources 1156, 1157, that in turn apply current to conductive load 1140 via electrodes 1114, 1115.

FIG. 14 shows hardware components of a voltage drive that includes a transformer. In FIG. 14, waveform generator 1101 outputs a voltage waveform that controls voltage-controlled voltage source 1151, that in turn applies a current to the primary wires of an isolation transformer 1108. Secondary wires of the transformer apply current to conductive load 1140 via electrodes 1111, 1112. Waveform generator 1102 outputs a voltage waveform that controls voltage-controlled voltage source 1106, that in turn applies current to conductive load 1140 via electrodes 1114, 1115.

In FIGS. 11, 12, 13, and 14, a computer (e.g., a microcontroller) 1131 controls the waveform generators 1101, 1102. The computer 1131 stores and retrieves data from memory device 1135. The computer 1131 interfaces with other hardware via a wired or fiber optic communication channel (e.g., a USB connection) 1132 or via a wireless module 1133. In some cases, a battery 1140 stores power and provides power to other components of the device. In some cases, one or more voltage regulators 1141 regulate voltage supplied to the device.

FIGS. 15A, 15B, 15C, 15D, 15E and 15F show examples of electrodes positioned on neuromodulation targets, in illustrative implementations of this invention. FIG. 15A shows a set of four electrodes 1501 positioned on the scalp 1503 of a head. FIG. 15B shows a set of four subdural electrodes 1511 positioned near a brain. FIG. 15C shows a neural probe 1521 inserted deep into a brain. FIG. 15D shows the tip 1523 of probe 1521. The probe tip includes four electrodes 1525, 1526, 1527, 1528. FIG. 15E shows a set of four transcutaneous electrodes 1531 positioned on the scalp of a head. FIG. 15F shows a set of four electrodes 1543 positioned on a nerve 1541.

In many embodiments of this invention, the electric fields generated by the first and second current channels, and any AM waveform created by interference of these electric fields, are periodic. Alternatively, one or more of these fields is aperiodic and the AM waveform created by their interference is aperiodic.

In illustrative embodiments, this invention may be used to advantage with implantable stimulating electrodes, such as electrodes 1525, 1526, 1527, 1528 shown in FIGS. 15D and 15E. In some embodiments of this invention: (a) implantable electrodes are implanted in a brain and create a high amplitude region that is path-connected and consists only of spatial points in the brain at which the largest envelope amplitude occurs; and (b) the minimum distance between the high amplitude region and the electrodes in the first and second pairs of electrodes is at least 0.9 times the minimum distance between the first and second pairs of electrodes.

Computers

In exemplary implementations of this invention, one or more electronic computers (e.g. 1131) are programmed and specially adapted: (1) to control the operation of, or interface with, hardware components of a current drive or voltage drive, including any waveform generators; (2) to perform any other calculation, computation, program, algorithm, computer function or computer task described or implied above; (3) to receive signals indicative of human input; (4) to output signals for controlling transducers for outputting information in human perceivable format; and (5) to process data, to perform computations, to execute any algorithm or software, and to control the read or write of data to and from memory devices. The one or more computers may be in any position or positions within or outside of the device. For example, in some cases (a) at least one computer is housed in or together with other components of the device, and (b) at least one computer is remote from other components of the device. The one or more computers are connected to each other or to other components in the device either: (a) wirelessly, (b) by wired connection, (c) by fiber-optic link, or (d) by a combination of wired, wireless or fiber optic links.

In exemplary implementations, one or more computers are programmed to perform any and all calculations, computations, programs, algorithms, computer functions and computer tasks described or implied above. For example, in some cases: (a) a machine-accessible medium has instructions encoded thereon that specify steps in a software program; and (b) the computer accesses the instructions encoded on the machine-accessible medium, in order to determine steps to execute in the program. In exemplary implementations, the machine-accessible medium comprises a tangible non-transitory medium. In some cases, the machine-accessible medium comprises (a) a memory unit or (b) an auxiliary memory storage device. For example, in some cases, a control unit in a computer fetches the instructions from memory.

In illustrative implementations, one or more computers execute programs according to instructions encoded in one or more tangible, non-transitory, computer-readable media. For example, in some cases, these instructions comprise instructions for a computer to perform any calculation, computation, program, algorithm, computer function or computer task described or implied above. For example, in some cases, instructions encoded in a tangible, non-transitory, computer-accessible medium comprise instructions for a computer to: 1) to control the operation of, or interface with, hardware components of a current drive or voltage drive, including any waveform generators; (2) to perform any other calculation, computation, program, algorithm, computer function or computer task described or implied above; (3) to receive signals indicative of human input; (4) to output signals for controlling transducers for outputting information in human perceivable format; and (5) to process data, to perform computations, to execute any algorithm or software, and to control the read or write of data to and from memory devices.

Definitions

The terms "a" and "an", when modifying a noun, do not imply that only one of the noun exists.

To say that an electric network is "anti-phasic" means that the network includes a first electrode and a second electrode and is configured to simultaneously create a first electrical waveform at the first electrode and a second electrical waveform at the second electrode, the first waveform having a first phase and the second waveform having a second phase, such that the difference between the first and second phases is substantially equal to 180 degrees.

The term "comprise" (and grammatical variations thereof) shall be construed as if followed by "without limitation". If A comprises B, then A includes B and may include other things.

The term "computer" includes any computational device that performs logical and arithmetic operations. For example, in some cases, a "computer" comprises an electronic computational device, such as an integrated circuit, a microprocessor, a mobile computing device, a laptop computer, a tablet computer, a personal computer, or a mainframe computer. In some cases, a "computer" comprises: (a) a central processing unit, (b) an ALU (arithmetic logic unit), (c) a memory unit, and (d) a control unit that controls actions of other components of the computer so that encoded steps of a program are executed in a sequence. In some cases, a "computer" also includes peripheral units including an auxiliary memory storage device (e.g., a disk drive or flash memory), or includes signal processing circuitry. However, a human is not a "computer", as that term is used herein.

"Defined Term" means a term or phrase that is set forth in quotation marks in this Definitions section.

For an event to occur "during" a time period, it is not necessary that the event occur throughout the entire time period. For example, an event that occurs during only a portion of a given time period occurs "during" the given time period.

The term "e.g." means for example.

The "envelope amplitude" of an amplitude-modulated waveform is equal to the peak amplitude of a signal, which signal is the top of the envelope of the amplitude-modulated waveform.

The fact that an "example" or multiple examples of something are given does not imply that they are the only instances of that thing. An example (or a group of examples) is merely a non-exhaustive and non-limiting illustration.

Unless the context clearly indicates otherwise: (1) a phrase that includes "a first" thing and "a second" thing does not imply an order of the two things (or that there are only two of the things); and (2) such a phrase is simply a way of identifying the two things, respectively, so that they each may be referred to later with specificity (e.g., by referring to "the first" thing and "the second" thing later). For example, unless the context clearly indicates otherwise, if an equation has a first term and a second term, then the equation may (or may not) have more than two terms, and the first term may occur before or after the second term in the equation. A phrase that includes a "third" thing, a "fourth" thing and so on shall be construed in like manner.

"For instance" means for example.

"Frequency" means fundamental frequency, unless the context explicitly indicates otherwise.

As used herein, to say that a thing (such as an object, event or fact) is "given" carries no implication regarding whether the thing is assumed, known or existing. As used herein, "given" simply identifies a thing (such as an object, event or fact), so that the thing may be referred to later with specificity.

"Ground" means electrical ground in an electrical circuit.

"Herein" means in this document, including text, specification, claims, abstract, and drawings.

As used herein: (1) "implementation" means an implementation of this invention; (2) "embodiment" means an embodiment of this invention; (3) "case" means an implementation of this invention; and (4) "use scenario" means a use scenario of this invention.

The term "include" (and grammatical variations thereof) shall be construed as if followed by "without limitation".

"Line segment" means a straight line segment.

"Load" means an electrical load in an electrical circuit.

An "output terminal" of a current source means a terminal from which, or into which, current created by the current source flows.

"Orthographic" refers to a projection in which each line of projection is perpendicular to a plane onto which the projection is being made.

"Node" means an electrical node in an electrical circuit.

To say that X is "out of" Y and Z means that X is a member of a set that consists of Y and Z.

The term "or" is inclusive, not exclusive. For example A or B is true if A is true, or B is true, or both A or B are true. Also, for example, a calculation of A or B means a calculation of A, or a calculation of B, or a calculation of A and B.

As used herein, "parameter" means a variable. For example: (a) if y=f(x), then both x and y are parameters; and (b) if z=f(x(t), y(t)), then t, x, y and z are parameters. A parameter may represent a physical quantity, such as pressure, temperature, or delay time.

A parenthesis is simply to make text easier to read, by indicating a grouping of words. A parenthesis does not mean that the parenthetical material is optional or may be ignored.

The term "path-connected" means path-connected, in the topological sense of the term.

As used herein, the term "set" does not include a group with no elements. Mentioning a first set and a second set does not, in and of itself, create any implication regarding whether or not the first and second sets overlap (that is, intersect). A set has one or more elements. As used herein, the phrase "set of _____", where the blank is filled in by any plural noun, means a "set of one or more _____". For example, a set of pencils means a set of one or more pencils.

To say that a first pair of electrodes and a second pair of electrodes are positioned "side-by-side" means that, for a first line segment that joins the electrodes of the first pair and a second line segment that joins the electrodes of the second pair, a geometric plane exists such that (i) the first line segment is positioned entirely on one side of the plane; (ii) the second line segment is positioned entirely on the other side of the plane; and (ii) neither the first line segment nor the second line segment intersect the plane.

"Some" means one or more.

To "stimulate" means to apply a stimulus or stimuli. The words "stimulate" and "stimulus" carry no implication regarding whether or how the person or thing being stimulated responds. For example, in some cases, a "stimulus" may evoke activity, suppress activity, or evoke no response.

As used herein, a "subset" of a set consists of less than all of the elements of the set.

"Substantially" means at least ten percent. For example: (a) 112 is substantially larger than 100; and (b) 108 is not substantially larger than 100.

To say that a first electric field and a second electric field are "substantially isolated from each other"—in a context where the first electric field is created by a first pair of electrodes, the second electric field is created by a second pair of electrodes, and the first and second pairs of electrodes are electrically connected to a common conductive load—means that a first ratio and a second ratio are each less than or equal to 0.07, where: (a) the first pair of electrodes comprises a first electrode and a second electrode; (b) the first ratio is a ratio of the magnitude of the highest magnitude frequency component of a second voltage to the magnitude of the highest magnitude frequency component of a first voltage; (c) the second pair of electrodes comprises a third electrode and a fourth electrode; (d) the second ratio is a ratio of the magnitude of the highest magnitude frequency component of a fourth voltage to the magnitude of the highest magnitude frequency component of a third voltage; (e) the first voltage is the voltage across the conductive load from the first electrode to the second electrode that is attributable to the first electric field; (f) the second voltage is the voltage across the conductive load from the first electrode to the second electrode that is attributable to the second electric field; (g) the third voltage is the voltage across the conductive load from the third electrode to the fourth electrode that is attributable to the second electric field; and (h) the fourth voltage is the voltage across the conductive load from the third electrode to the fourth electrode that is attributable to the second electric field.

The term "such as" means for example.

To say that a first electric field and second electric field are "temporally asymmetric means that: (a) the first electrical field is a periodic waveform that has a first rise time and a first fall time; (b) the second electrical field is a periodic waveform that has a second rise time and a second fall time; and (c) either: (i) the first rise time is longer than the first fall time and the second rise time is shorter than the second fall time, or (ii) the first rise time is shorter than the first fall time and the second rise time is longer than the second fall time.

The term "waveform" carries no implication regarding whether the waveform is periodic. A waveform may be either periodic or aperiodic.

Except to the extent that the context clearly requires otherwise, if steps in a method are described herein, then the method includes variations in which: (1) steps in the method occur in any order or sequence, including any order or sequence different than that described; (2) any step or steps in the method occurs more than once; (3) different steps, out of the steps in the method, occur a different number of times during the method, (4) any combination of steps in the method is done in parallel or serially; (5) any step or steps in the method is performed iteratively; (6) a given step in the method is applied to the same thing each time that the given step occurs or is applied to different things each time that the given step occurs; or (7) the method includes other steps, in addition to the steps described.

This Definitions section shall, in all cases, control over and override any other definition of the Defined Terms. For example, the definitions of Defined Terms set forth in this Definitions section override common usage or any external dictionary. If a given term is explicitly or implicitly defined in this document, then that definition shall be controlling, and shall override any definition of the given term arising from any source (e.g., a dictionary or common usage) that is external to this document. If this document provides clarification regarding the meaning of a particular term, then that clarification shall, to the extent applicable, override any definition of the given term arising from any source (e.g., a dictionary or common usage) that is external to this document. To the extent that any term or phrase is defined or clarified herein, such definition or clarification applies to any grammatical variation of such term or phrase, taking into account the difference in grammatical form. For example, the grammatical variations include noun, verb, participle, adjective, and possessive forms, and different declensions, and different tenses. In each case described in this paragraph, the Applicant or Applicants are acting as his, her, its or their own lexicographer.

Variations

This invention may be implemented in many different ways. Here are some non-limiting examples:

In one aspect, this invention is a method comprising: (a) a first electrical network creating a first electric field between electrodes in a first pair of electrodes; and (b) a second electrical network creating a second electric field between electrodes in a second pair of electrodes, such that (i) the first and second electric fields constructively and destructively interfere with each other to create an amplitude-modulated waveform and (ii) the largest envelope amplitude of the amplitude-modulated waveform occurs in a brain; wherein, during steps (a) and (b) above, the first and second electrode pairs are electrically connected to the brain. In some cases, the first electrode pair and second electrode pair are positioned side-by-side. In some cases: (a) the amplitude modulated waveform has an envelope amplitude; and (b) the first electrode pair and second electrode pair are positioned such that, at a given time, the largest magnitude of the envelope amplitude occurs in only one region of the brain, which region is path-connected and consists only of those points at which the magnitude of the envelope amplitude is equal to the largest magnitude. In some cases, the region spatially coincides with cortical tissue of the brain. In some cases, the region spatially coincides with subcortical tissue of the brain. In some cases: (a) the amplitude modulated waveform has an envelope amplitude; (b) the greatest magnitude of the envelope amplitude occurs in a spatial position in the brain; (c) a volume exists, which volume consists of only those points at which the magnitude of the envelope amplitude is equal to at least 50% of the greatest magnitude; and (d) this volume coincides with both cortical and subcortical tissue of the brain. In some cases: (a) the first electrical network comprises a first waveform generator, a first set of one or more dependent current sources, and a first pair of electrodes, (b) the first waveform generator controls the first set of current sources, (c) the first set of current sources creates an electrical current that flows through the first pair of electrodes; (d) the second electrical network comprises a second waveform generator, a second set of one or more dependent current sources, and a second pair of electrodes, (e) the second waveform generator controls the second set of current sources, and (f) the second set of current sources creates an electrical current that flows through the second pair of electrodes. In some cases, at least one of the first and second electrical networks is anti-phasic. In some cases: (a) the first set of current sources comprises a first current source and a second current source; (b) a positive input terminal of the first current source is electrically connected to the first waveform generator and a negative input terminal of the first current source is electrically connected to ground; and (c) a negative input terminal of the second current source is electrically connected to the first waveform generator and a positive input terminal of the second current source is electrically connected to ground. In some cases: (a) the first and second pairs of electrodes are implanted inside the brain; and (b) the minimum distance between the region and the electrodes in the first and second pairs of electrodes is at least 0.9 times the minimum distance between the first and second pairs of electrodes. In some cases: (a) a resistor is connected to ground; and (c) an electrode, out of the first and second pairs of electrodes, share a common node. In some cases: the method includes an additional electrode that it configured to be electrically connected to both the load and ground while the first and second electrode pairs are electrically connected to the load. In some cases: (a) a given electrical network, out of the first and second networks, includes a transformer; (b) a secondary wire of the transformer is electrically connected to an electrode in the first pair of electrodes; (c) another secondary wire of the transformer is electrically connected to another electrode in the first pair of electrodes; (d) the first set of current sources includes a given current source; (e) a primary wire of the transformer is connected an output terminal of the given current source; and (f) another primary wire of the transformer is connected another output terminal of the give current source. In some cases, the amplitude-modulated waveform entrains neurons in a portion of the brain. In some cases: (a) the amplitude-modulated waveform includes a sequence of peaks; and (b) the amplitude-modulated waveform stimulates neurons in at least a portion of the brain such that the neurons undergo a sequence of action potentials that is time-locked to the sequence of peaks. In some cases: (a) the amplitude-modulated waveform has an envelope that has a top and a bottom; and (b) the difference between the voltage at the top and the voltage at the bottom is not equal to zero during at least part of the amplitude-modulated waveform. In some cases: (a) a given electrical field, out of the first and second electrical fields, is periodic; and (b) the integral of the voltage of the given electrical field, over an entire period of the electrical field, is equal to zero relative to earth ground. In some cases, the first and second electric fields are temporally asymmetric. In some cases, a given current source, out of the first and second sets of current sources, has an internal resistance greater than one mega-ohm in the compliance voltage range of the given current source. In some cases, the first and second electric fields are aperiodic. In some cases, the first and second electrical fields are substantially isolated from each other even though (i) the first and second pairs of electrodes are electrically connected to the brain and (ii) each of the fields extends through all of the brain. Each of the cases described above in this paragraph is an example of the method described in the first sentence of this paragraph, and is also an example of an embodiment of this invention that may be combined with other embodiments of this invention.

In another aspect, this invention is an apparatus comprising: (a) a first electrical network for creating a first electric field between electrodes in a first pair of electrodes; and (b) a second electrical network for creating a second electric field between electrodes in a second pair of electrodes, such that (i) when the first and second pairs of electrodes are electrically connected to a brain, the first and second electric fields constructively and destructively interfere with each other to create an amplitude-modulated waveform, and (ii) the largest envelope amplitude of the amplitude-modulated waveform occurs in the brain. In some cases, the first electrode pair and second electrode pair are configured to be positioned side-by-side. In some cases, the first electrode pair and second electrode pair are configured to be positioned such that, at a given time, the largest magnitude of the envelope amplitude occurs in only one region of the brain, which region is path-connected and consists only of those points at which the magnitude of the envelope amplitude is equal to the largest magnitude. In some cases, the region spatially coincides with cortical tissue of the brain. In some cases, the region spatially coincides with subcortical tissue of the brain. In some cases: (a) the amplitude modulated waveform has an envelope amplitude; (b) the greatest magnitude of the envelope amplitude occurs in a spatial position in the brain; (c) a volume exists, which volume consists of only those points at which the magnitude of the envelope amplitude is equal to at least 50% of the greatest magnitude; and (d) this volume coincides with both cortical and subcortical tissue of the brain. In some cases: (a) the first electrical network comprises a first waveform generator, a first set of one or more dependent current sources, and a first pair of electrodes, (b) the first waveform generator is configured to control the first set of current sources, (c) the first set of current sources is configured to create one or more electrical currents such that the first pair of electrodes creates the first electrical field, (d) the second electrical network comprises a second waveform generator, a second set of one or more dependent current sources, and a second pair of electrodes, (e) the second waveform generator is configured to control the second set of current sources, and (f) the second set of current sources is configured to create one or more electrical currents such that the second pair of electrodes creates the second electrical field. In some cases, at least one of the first and second electrical networks is anti-phasic. 30. In some cases: (a) the first set of current sources comprises a first current source and a second current source; b) a positive input terminal of the first current source is electrically connected to the first waveform generator and a negative input terminal of the first current source is electrically connected to ground; and (c) a negative input terminal of the second current source is electrically connected to the first waveform generator and a positive input terminal of the second current source is electrically connected to ground. In some cases, the first and second pairs of electrodes are configured to be implanted inside the brain, such that, at a time when the first and second pairs of electrodes are implanted inside the brain, the minimum distance between the region and the electrodes in the first and second pairs of electrodes is at least 0.9 times the minimum distance between the first and second pairs of electrodes. In some cases: (a) a resistor is connected to ground; and (b) an electrode, out of the first and second pairs of electrodes, share a common node. In some cases, the apparatus includes an additional electrode that it configured to be electrically connected to both the load and ground while the first and second electrode pairs are electrically connected to the load. In some cases: (a) a given electrical network, out of the first and second networks, includes a transformer; (b) a secondary wire of the transformer is electrically connected to an electrode in the first pair of electrodes; (c) another secondary wire of the transformer is electrically connected to another electrode in the first pair of electrodes; (d) the first set of current sources includes a given current source; (e) a primary wire of the transformer is connected an output terminal of the given current source; and (f) another primary wire of the transformer is connected another output terminal of the give current source. In some cases, the amplitude-modulated waveform entrains neurons in a portion of the brain. In some cases, (a) the amplitude-modulated waveform includes a sequence of peaks; and (b) the amplitude-modulated waveform stimulates neurons in at least a portion of the brain such that the neurons undergo a sequence of action potentials that is time-locked to the sequence of peaks. In some cases: (a) the amplitude-modulated waveform has an envelope that has a top and a bottom; and (b) the difference between the voltage at the top and the voltage at the bottom is not equal to zero during at least part of the amplitude-modulated waveform. In some cases: (a) a given electrical field, out of the first and second electrical fields, is periodic; and (b) the integral of the voltage of the given electrical field, over an entire period of the electrical field, is equal to zero relative to earth ground. In some cases, the first and second electric fields are temporally asymmetric. In some cases, a given current source, out of the first and second sets of current sources, has an internal resistance greater than one mega-ohm in the compliance voltage range of the given current source. In some cases, the first and second electric fields are aperiodic. In some cases, when the first and second pairs of electrodes are electrically connected to the brain, the first and second electrical fields are substantially isolated from each other even though each of the fields extends through all of the brain. Each of the cases described above in this paragraph is an example of the apparatus described in the first sentence of this paragraph, and is also an example of an embodiment of this invention that may be combined with other embodiments of this invention.

In another aspect, this invention is a method comprising: (a) a first electrical network creating a first electrical field between electrodes in a first pair of electrodes; and (b) a second electrical network creating a second electrical field between electrodes in a second pair of electrodes, the first and second pairs of electrodes being electrically connected to a common conductive load; wherein (i) at least one of the electrical networks is anti-phasic, (ii) the first electrical network comprises a first waveform generator, a first set of one or more dependent current sources, and a first pair of electrodes, (iii) the first waveform generator controls the first set of current sources, (iv) the first set of current sources creates an electrical current that flows through the first pair of electrodes; (v) the second electrical network comprises a second waveform generator, a second set of one or more dependent current sources, and a second pair of electrodes, (vi) the second waveform generator controls the second set of current sources, and (vii) the second set of current sources creates an electrical current that flows through the second pair of electrodes. In some cases: (a) the first set of current sources comprises a first current source and a second current source; (b) a positive input terminal of the first current source is electrically connected to the first waveform generator and a negative input terminal of the first current source is electrically connected to ground; and (c) a negative input terminal of the second current source is electrically connected to the first waveform generator and a positive input terminal of the second current source is electrically connected to ground. In some cases: (a) the second set of current sources comprises a third current source and a fourth current source; (b) a positive input terminal of the third current source is electrically connected to the second waveform generator and a negative input terminal of the third current source is electrically connected to ground; and (c) a negative input terminal of the fourth current source is electrically connected to the second waveform generator and a positive input terminal of the fourth current source is electrically connected to ground. In some cases: a) a resistor is connected to ground; and (b) an electrode, out of the first and second pairs of electrodes, share a common node. In some cases, the first and second sets of current sources comprise voltage-controlled current sources. In some cases, a given current source, out of the first and second sets of current sources, has an internal resistance greater than one mega-ohm in the compliance voltage range of the given current source. In some cases, the first and second electric fields are aperiodic. In some cases, the first and second electrical fields are substantially isolated from each other even though (i) the first and second electrical pairs are electrically connected to the conductive load, and (ii) each of the fields extends through all of the conductive load. In some cases, the common conductive load includes a brain. In some cases: (a) neurons in a first region of the brain entrain to the first electrical field and not to the second electrical field; and (b) neurons in the second region of the brain entrain to the second electrical field and not to the first electrical field. In some cases: (a) the first and second electric fields constructively and destructively interfere with each other to create an amplitude-modulated waveform in the brain; and (b) at least some neurons in the brain entrain to the amplitude-modulated waveform. Each of the cases described above in this paragraph is an example of the method described in the first sentence of this paragraph, and is also an example of an embodiment of this invention that may be combined with other embodiments of this invention.

In another aspect, this invention is an apparatus comprising: (a) a first electrical network for creating a first electrical field between electrodes in a first pair of electrodes; and (b) a second electrical network for creating a second electrical field between electrodes in a second pair of electrodes, the first and second pairs of electrodes being configured to be electrically connected to a common conductive load; wherein (i) at least one of the electrical networks is antiphasic, (ii) the first electrical network comprises a first waveform generator, a first set of one or more dependent current sources, and a first pair of electrodes, (iii) the first waveform generator is configured to control the first set of current sources, (iv) the first set of current sources is configured to create an electrical current that flows through the first pair of electrodes, (v) the second electrical network comprises a second waveform generator, a second set of one or more dependent current sources, and a second pair of electrodes, (vi) the second waveform generator is configured to control the second set of current sources, and (vii) the second set of current sources is configured to create an electrical current that flows through the second pair of electrodes. In some cases: (a) the first set of current sources comprises a first current source and a second current source; (b) a positive input terminal of the first current source is electrically connected to the first waveform generator and a negative input terminal of the first current source is electrically connected to ground; and (c) a negative input terminal of the second current source is electrically connected to the first waveform generator and a positive input terminal of the second current source is electrically connected to ground. In some cases: (a) the second set of current sources comprises a third current source and a fourth current source; (b) a positive input terminal of the third current source is electrically connected to the second waveform generator and a negative input terminal of the third current source is electrically connected to ground; and (c) a negative input terminal of the fourth current source is electrically connected to the second waveform generator and a positive input terminal of the fourth current source is electrically connected to ground. In some cases: a) a resistor is connected to ground; and (b) an electrode, out of the first and second pairs of electrodes, share a common node. In some cases, the first and second sets of current sources comprise voltage-controlled current sources. In some cases, a given current source, out of the first and second sets of current sources, has an internal resistance greater than one mega-ohm in the compliance voltage range of the given current source In some cases, the first and second electric fields are aperiodic. In some cases, when the first and second pairs of electrodes are electrically connected to the conductive load, the first and second electrical fields are substantially isolated from each other even though each of the fields extends through all of the conductive load. In some cases, the common conductive load includes a brain. In some cases, when the first and second pairs of electrodes are electrically connected to the brain: (a) neurons in a first region of the brain entrain to the first electrical field and not to the second electrical field; and (b) neurons in the second region of the brain entrain to the second electrical field and not to the first electrical field. In some cases, when the first and second pairs of electrodes are electrically connected to the brain: (a) the first and second electric fields constructively and destructively interfere with each other to create an amplitude-modulated waveform in the brain; and (b) at least some neurons in the brain entrain to the amplitude-modulated waveform. Each of the cases described above in this paragraph is an example of the apparatus described in the first sentence of this paragraph, and is also an example of an embodiment of this invention that may be combined with other embodiments of this invention.

In another aspect, this invention is a method comprising: (a) a first electrical network creating a first electric field between electrodes in a first pair of electrodes; and (b) a second electrical network creating a second electric field between electrodes in a second pair of electrodes, such that (i) the first and second electric fields constructively and destructively interfere with each other to create an amplitude-modulated waveform and (ii) the largest envelope amplitude of the amplitude-modulated waveform occurs in a heart; wherein, during steps (a) and (b) of this sentence, the first and second electrode pairs are electrically connected to the heart. In some cases, the first electrode pair and second electrode pair are positioned side-by-side. In some cases: (a) the amplitude modulated waveform has an envelope amplitude; and (b) the first electrode pair and second electrode pair are positioned such that, at a given time, the largest magnitude of the envelope amplitude occurs in only one region of the heart, which region is path-connected and consists only of those points at which the magnitude of the envelope amplitude is equal to the largest magnitude. In some cases: (a) the first electrical network comprises a first waveform generator, a first set of one or more dependent current sources, and a first pair of electrodes, (b) the first waveform generator controls the first set of current sources, (c) the first set of current sources creates an electrical current that flows through the first pair of electrodes; (d) the second electrical network comprises a second waveform generator, a second set of one or more dependent current sources, and a second pair of electrodes, (e) the second waveform generator controls the second set of current sources, and (f) the second set of current sources creates an electrical current that flows through the second pair of electrodes. In some cases, at least one of the first and second electrical networks is anti-phasic. In some cases: (a) the first set of current sources comprises a first current source and a second current source; (b) a positive input terminal of the first current source is electrically connected to the first waveform generator and a negative input terminal of the first current source is electrically connected to ground; and (c) a negative input terminal of the second current source is electrically connected to the first waveform generator and a positive input terminal of the second current source is electrically connected to ground. Each of the cases described above in this paragraph is an example of the method described in the first sentence of this paragraph, and is also an example of an embodiment of this invention that may be combined with other embodiments of this invention.

In another aspect, this invention is an apparatus comprising: (a) a first electrical network for creating a first electric field between electrodes in a first pair of electrodes; and (b) a second electrical network for creating a second electric field between electrodes in a second pair of electrodes, such that (i) when the first and second pairs of electrodes are electrically connected to a heart, the first and second electric fields constructively and destructively interfere with each other to create an amplitude-modulated waveform, and (ii) the largest envelope amplitude of the amplitude-modulated waveform occurs in the heart. In some cases, the first electrode pair and second electrode pair are configured to be positioned side-by-side. In some cases, the first electrode pair and second electrode pair are configured to be positioned such that, at a given time, the largest magnitude of the envelope amplitude occurs in only one region of the heart, which region is path-connected and consists only of those points at which the magnitude of the envelope amplitude is equal to the largest magnitude. In some cases: (a) the first electrical network comprises a first waveform generator, a first set of one or more dependent current sources, and a first pair of electrodes, (b) the first waveform generator is configured to control the first set of current sources, (c) the first set of current sources is configured to create one or more electrical currents such that the first pair of electrodes creates the first electrical field, (d) the second electrical network comprises a second waveform generator, a second set of one or more dependent current sources, and a second pair of electrodes, (e) the second waveform generator is configured to control the second set of current sources, and (f) the second set of current sources is configured to create one or more electrical currents such that the second pair of electrodes creates the second electrical field. In some cases, at least one of the first and second electrical networks is anti-phasic. In some cases: (a) the first set of current sources comprises a first current source and a second current source; (b) a positive input terminal of the first current source is electrically connected to the first waveform generator and a negative input terminal of the first current source is electrically connected to ground; and (c) a negative input terminal of the second current source is electrically connected to the first waveform generator and a positive input terminal of the second current source is electrically connected to ground. Each of the cases described above in this paragraph is an example of the apparatus described in the first sentence of this paragraph, and is also an example of an embodiment of this invention that may be combined with other embodiments of this invention.

In another aspect, this invention is a method comprising: (a) a first electrical network creating a first electric field between electrodes in a first pair of electrodes; and (b) a second electrical network creating a second electric field between electrodes in a second pair of electrodes, such that (i) the first and second electric fields constructively and destructively interfere with each other to create an amplitude-modulated waveform and (ii) the largest envelope amplitude of the amplitude-modulated waveform occurs in a nerve; wherein, during steps (a) and (b) of this claim 1, the first and second electrode pairs are electrically connected to the nerve. In some cases, the first electrode pair and second electrode pair are positioned side-by-side. In some cases: (a) the amplitude modulated waveform has an envelope amplitude; and (b) the first electrode pair and second electrode pair are positioned such that, at a given time, the largest magnitude of the envelope amplitude occurs in only one region of the nerve, which region is path-connected and consists only of those points at which the magnitude of the envelope amplitude is equal to the largest magnitude. In some cases: (a) the first electrical network comprises a first waveform generator, a first set of one or more dependent current sources, and a first pair of electrodes, (b) the first waveform generator controls the first set of current sources, (c) the first set of current sources creates an electrical current that flows through the first pair of electrodes; (d) the second electrical network comprises a second waveform generator, a second set of one or more dependent current sources, and a second pair of electrodes, (e) the second waveform generator controls the second set of current sources, and (f) the second set of current sources creates an electrical current that flows through the second pair of electrodes. In some cases, at least one of the first and second electrical networks is anti-phasic. In some cases: (a) the first set of current sources comprises a first current source and a second current source; (b) a positive input terminal of the first current source is electrically connected to the first waveform generator and a negative input terminal of the first current source is electrically connected to ground; and (c) a negative input terminal of the second current source is electrically connected to the first waveform generator and a positive input terminal of the second current source is electrically connected to ground. Each of the cases described above in this paragraph is an example of the method described in the first sentence of this paragraph, and is also an example of an embodiment of this invention that may be combined with other embodiments of this invention.

In another aspect, this invention is an apparatus comprising: (a) a first electrical network for creating a first electric field between electrodes in a first pair of electrodes; and (b) a second electrical network for creating a second electric field between electrodes in a second pair of electrodes, such that (i) when the first and second pairs of electrodes are electrically connected to a nerve, the first and second electric fields constructively and destructively interfere with each other to create an amplitude-modulated waveform, and (ii) the largest envelope amplitude of the amplitude-modulated waveform occurs in the nerve. In some cases, the first electrode pair and second electrode pair are configured to be positioned side-by-side. In some cases, the first electrode pair and second electrode pair are configured to be positioned such that, at a given time, the largest magnitude of the envelope amplitude occurs in only one region of the nerve, which region is path-connected and consists only of those points at which the magnitude of the envelope amplitude is equal to the largest magnitude. In some cases: (a) the first electrical network comprises a first waveform generator, a first set of one or more dependent current sources, and a first pair of electrodes, (b) the first waveform generator is configured to control the first set of current sources, (c) the first set of current sources is configured to create one or more electrical currents such that the first pair of electrodes creates the first electrical field, (d) the second electrical network comprises a second waveform generator, a second set of one or more dependent current sources, and a second pair of electrodes, (e) the second waveform generator is configured to control the second set of current sources, and (f) the second set of current sources is configured to create one or more electrical currents such that the second pair of electrodes creates the second electrical field. In some cases, at least one of the first and second electrical networks is anti-phasic. In some cases: (a) the first set of current sources comprises a first current source and a second current source; (b) a positive input terminal of the first current source is electrically connected to the first waveform generator and a negative input terminal of the first current source is electrically connected to ground; and (c) a negative input terminal of the second current source is electrically connected to the first waveform generator and a positive input terminal of the second current source is electrically connected to ground. Each of the cases described above in this paragraph is an example of the apparatus described in the first sentence of this paragraph, and is also an example of an embodiment of this invention that may be combined with other embodiments of this invention.

The above description (including without limitation any attached drawings and figures) describes illustrative implementations of the invention. However, the invention may be implemented in other ways. The methods and apparatus which are described above are merely illustrative applications of the principles of the invention. Other arrangements, methods, modifications, and substitutions by one of ordinary skill in the art are therefore also within the scope of the present invention. Numerous modifications may be made by those skilled in the art without departing from the scope of the invention. Also, this invention includes without limitation each combination and permutation of one or more of the abovementioned implementations, embodiments and features.

What is claimed:

1. A method comprising:
   (a) creating a first electric field between a first pair of electrodes and creating a second electric field between a second pair of electrodes, in such a way that the first and second electric fields constructively and destructively interfere with each other to create an amplitude-modulated waveform, which waveform has an envelope amplitude; and
   (b) controlling location of a spatial position at which the envelope amplitude of the waveform is greatest, in such a way that the spatial position is located in biological tissue.

2. The method of claim 1, wherein the first and second pairs of electrodes are positioned in such a way that:
   (a) the first pair of electrodes is positioned entirely on one side of a geometric plane;
   (b) the second pair of electrodes is positioned entirely on another side of the geometric plane; and
   (c) the geometric plane intersects the biological tissue.

3. The method of claim 1, wherein distance between electrodes in the first pair of electrodes is different than distance between electrodes in the second pair of electrodes.

4. The method of claim 1, wherein the first electrode pair is anti-phasic.

5. The method of claim 1, wherein:
   (a) the envelope amplitude exceeds a given threshold in a region; and
   (b) the method includes controlling size, shape and position of the region by adjusting relative amplitudes of the first and second electric fields and by adjusting placement of the first and second pairs of electrodes.

6. The method of claim 1, wherein:
   (a) the first and second pairs of electrodes are implanted inside a body, which body includes the tissue;
   (b) the minimum distance between a region and the electrodes in the first and second pairs of electrodes is at least 0.9 times the minimum distance between the first and second pairs of electrodes; and
   (c) the region consists of only those points at which the magnitude of the envelope amplitude is greatest.

7. The method of claim 1, wherein the first and second electric fields are temporally asymmetric.

8. The method of claim 1, wherein the first and second electric fields are aperiodic.

9. The method of claim 1, wherein the biological tissue comprises a spinal cord.

10. The method of claim 1, wherein the biological tissue comprises a nerve.

11. The method of claim 1, wherein the biological tissue comprises a muscle or a gland.

12. The method of claim 1, wherein the biological tissue comprises reproductive tissue or tissue in a digestive tract.

13. An apparatus comprising:
   (a) a first electrical network; and
   (b) a second electrical network;
   wherein
   (i) the first electrical network includes a first pair of electrodes,
   (ii) the second electrical network includes a second pair of electrodes,
   (iii) the first electrical network is configured to create a first electric field between the first pair of electrodes and the second electrical network is configured to create a second electric field between the second pair of electrodes, in such a way that the first and second electric fields constructively and destructively interfere with each other to create an amplitude-modulated waveform, which waveform has an envelope amplitude, and
   (iv) the apparatus is configured to control location of a spatial position at which the envelope amplitude of the waveform is greatest, in such a way that the spatial position is located in biological tissue.

14. The apparatus of claim 13, wherein the apparatus is configured in such a way that relative amplitudes of the first and second electric fields produced by the apparatus are adjustable.

15. The apparatus of claim 13, wherein at least one of the first and second electric networks is anti-phasic.

16. The apparatus of claim 13, wherein the first and second electric fields are aperiodic.

17. The apparatus of claim 13, wherein the biological tissue comprises a spinal cord.

18. The apparatus of claim 13, wherein the biological tissue comprises a nerve.

19. The apparatus of claim 13, wherein the biological tissue comprises a muscle or a gland.

20. The apparatus of claim 13, wherein the biological tissue comprises reproductive tissue or tissue in a digestive tract.

\* \* \* \* \*